US012419520B2

(12) United States Patent
Newhouse et al.

(10) Patent No.: US 12,419,520 B2
(45) Date of Patent: Sep. 23, 2025

(54) WEARABLE DEVICE

(71) Applicant: Chamartin Laboratories LLC, Wilmington, DE (US)

(72) Inventors: Todd Andrew Newhouse, Escondido, CA (US); Evan Einbender Aamodt, Philadelphia, PA (US); Hooman Abediasl, Thousand Oaks, CA (US); Adrian Williamson Bahani, Garden Grove, CA (US); Kate LeeAnn Bechtel, Pleasant Hill, CA (US); Renata Melamud Berger, Palo Alto, CA (US); Patrick John Castagna, Escondido, CA (US); Suresh Chengalva, Carmel, IN (US); Lok Man Chu, San Marino, CA (US); Jennifer Lynn Corso, Peoria, AZ (US); Cristiano Dalvi, Lake Forest, CA (US); Jeffrey Driscoll, San Jose, CA (US); Alexander Fast, Aliso Viejo, CA (US); Craig Gadd, Lemon Grove, CA (US); Alexander Gondarenko, San Jose, CA (US); Richard Grote, Rancho Cucamonga, CA (US); Christopher Alan Harris, Fort Collins, CO (US); Vafa Jamali, Boulder, CO (US); Haydn Frederick Jones, London (GB); Vishwas Kulkarni, Pasadena, CA (US); Ferdyan Lesmana, Foothill Ranch, CA (US); Sean Merritt, Lake Forest, CA (US); Roozbeh Parsa, Portola Valley, CA (US); Philip Perea, Aliso Viejo, CA (US); Kyle Rick, Boulder, CO (US); Andrew George Rickman, Marlborough (GB); Adam Scofield, Los Angeles, CA (US); Breanna Stachowski, Elma, NY (US); Benjamin Ver Steeg, Redlands, CA (US); Guomin Yu, Glendora, CA (US); Aaron John Zilkie, Pasadena, CA (US)

(73) Assignee: Chamartin Laboratories LLC, Wilmington, DE (US)

( * ) Notice: Subject to any disclaimer, the term of this patent is extended or adjusted under 35 U.S.C. 154(b) by 0 days.

(21) Appl. No.: 18/451,099

(22) Filed: Aug. 16, 2023

(65) Prior Publication Data
US 2023/0397818 A1    Dec. 14, 2023

Related U.S. Application Data

(63) Continuation-in-part of application No. 18/263,324, filed as application No. PCT/IB2022/000050 on Feb.
(Continued)

(51) Int. Cl.
*A61B 5/00*    (2006.01)

(52) U.S. Cl.
CPC .......... *A61B 5/0075* (2013.01); *A61B 5/681* (2013.01); *A61B 5/6831* (2013.01)

(58) Field of Classification Search
CPC ......... A61B 5/0075; A61B 5/01; A61B 5/021; A61B 5/02405; A61B 5/02427;
(Continued)

(56) References Cited

U.S. PATENT DOCUMENTS

| 5,273,036 A | 12/1993 | Kronberg et al. |
| 6,031,603 A | 2/2000 | Fine et al. |

(Continued)

FOREIGN PATENT DOCUMENTS

EP    2 898 822 A1    7/2015

OTHER PUBLICATIONS

Hanson, M.A. et al., "Body Area Sensor Networks: Challenges and Opportunities", IEEE Computer Society, Jan. 2009, pp. 58-65, IEEE.
(Continued)

*Primary Examiner* — George Manuel
(74) *Attorney, Agent, or Firm* — Brownstein Hyatt Farber Schreck, LLP

(57) ABSTRACT

A wearable device. In some embodiments, the wearable device includes: a sensing module; and a strap attached to
(Continued)

the sensing module, the wearable device being configured to be worn by a user, with a lower surface of the sensing module in contact with the user, the strap extending over an upper surface of the sensing module.

18 Claims, 29 Drawing Sheets

Related U.S. Application Data 3, 2022, and a continuation-in-part of application No. 17/757,130, filed as application No. PCT/IB2020/001037 on Dec. 11, 2020, now Pat. No. 11,766,216.

(60) Provisional application No. 63/373,853, filed on Aug. 29, 2022, provisional application No. 63/371,732, filed on Aug. 17, 2022, provisional application No. 63/151,521, filed on Feb. 19, 2021, provisional application No. 63/146,325, filed on Feb. 5, 2021, provisional application No. 63/081,818, filed on Sep. 22, 2020, provisional application No. 63/078,828, filed on Sep. 15, 2020, provisional application No. 63/075,645, filed on Sep. 8, 2020, provisional application No. 63/060,581, filed on Aug. 3, 2020, provisional application No. 63/016,897, filed on Apr. 28, 2020, provisional application No. 62/946,929, filed on Dec. 11, 2019, provisional application No. 62/946,813, filed on Dec. 11, 2019, provisional application No. 62/946,860, filed on Dec. 11, 2019.

(58) Field of Classification Search
CPC .............. A61B 5/02438; A61B 5/0816; A61B 5/14532; A61B 5/1455; A61B 5/14551; A61B 5/4875; A61B 5/681; A61B 5/6831
See application file for complete search history.

(56) References Cited

U.S. PATENT DOCUMENTS

| | | |
|---|---|---|
| 9,392,946 B1 | 7/2016 | Sarantos et al. |
| 11,266,320 B2 | 3/2022 | Block et al. |
| 11,536,653 B2 | 12/2022 | Han et al. |
| 11,717,197 B2 | 8/2023 | Venugopal et al. |
| 2002/0042558 A1 | 4/2002 | Mendelson |
| 2008/0297788 A1 | 12/2008 | Rowe et al. |
| 2009/0182208 A1 | 7/2009 | Cho et al. |
| 2010/0026995 A1 | 2/2010 | Merritt et al. |
| 2012/0150047 A1 | 6/2012 | Terumoto et al. |
| 2013/0060098 A1 | 3/2013 | Thomsen et al. |
| 2014/0183342 A1 | 7/2014 | Shedletsky et al. |
| 2014/0371601 A1 | 12/2014 | Fei |
| 2015/0173633 A1 | 6/2015 | Shimizu et al. |
| 2015/0355604 A1 | 12/2015 | Fraser et al. |
| 2016/0022178 A1 | 1/2016 | Wang |
| 2016/0058312 A1 | 3/2016 | Han et al. |
| 2016/0235364 A1 | 8/2016 | Yoshida et al. |
| 2016/0287103 A1 | 10/2016 | Saponas et al. |
| 2016/0310027 A1 | 10/2016 | Han |
| 2017/0150305 A1* | 5/2017 | Chaudhri .......... H04M 1/72412 |
| 2017/0164848 A1 | 6/2017 | Nadeau et al. |
| 2017/0347902 A1 | 12/2017 | Van Gool et al. |
| 2018/0113911 A1 | 4/2018 | Ikeda et al. |
| 2019/0069781 A1 | 3/2019 | Kim et al. |
| 2022/0167889 A1 | 6/2022 | Kriegstein et al. |
| 2022/0183569 A1 | 6/2022 | Vule et al. |
| 2022/0216659 A1 | 7/2022 | Xu et al. |
| 2024/0074667 A1 | 3/2024 | Rick et al. |

OTHER PUBLICATIONS

International Search Report and Written Opinion of the International Searching Authority, mailed Jan. 30, 2024, corresponding to PCT/IB2023/000497, 16 pages.

Invitation to Pay Additional Fees, mailed Nov. 24, 2023 in related International Application No. PCT/IB2023/000497, 12 pages.

\* cited by examiner

Cross section view with lid shown

WEARABLE DEVICE

CROSS-REFERENCE TO RELATED APPLICATION(S)

The present application is a continuation-in-part of U.S. patent application Ser. No. 17/757,130, filed Jun. 9, 2022, which is a national stage application of International Patent Application No. PCT/IB2020/001037, filed Dec. 11, 2020, which claims priority to U.S. Provisional Patent Application No. 62/946,813, filed Dec. 11, 2019, and to U.S. Provisional Patent Application No. 62/946,860, filed Dec. 11, 2019, and to U.S. Provisional Patent Application No. 62/946,929, filed Dec. 11, 2019, and to U.S. Provisional Patent Application No. 63/016,897, filed Apr. 28, 2020, and to U.S. Provisional Patent Application No. 63/060,581, filed Aug. 3, 2020, and to U.S. Provisional Patent Application No. 63/075,645, filed Sep. 8, 2020, and to U.S. Provisional Patent Application No. 63/078,828, filed Sep. 15, 2020, and to U.S. Provisional Patent Application No. 63/081,818, filed Sep. 22, 2020; the present application is a continuation-in-part of U.S. patent application Ser. No. 18/263,324, filed Jul. 27, 2023, which is a national stage application of International Patent Application No. PCT/IB2022/000050, filed Feb. 3, 2022, which claims priority to U.S. Provisional Patent Application No. 63/146,325, filed Feb. 5, 2021, and to U.S. Provisional Patent Application No. 63/151,521, filed Feb. 19, 2021; the present application claims the benefit of U.S. Provisional Patent Application No. 63/371,732, filed Aug. 17, 2022, and of U.S. Provisional Patent Application No. 63/373,853, filed Aug. 29, 2022. The entire contents of all of the applications identified in this paragraph are incorporated herein by reference.

FIELD

One or more aspects of embodiments according to the present disclosure relate to health monitoring, and more particularly to a wearable device for health monitoring.

BACKGROUND

In various circumstances it may be advantageous to monitor various aspects of the health state of a subject or patient periodically or continuously, without a need for the patient to visit a clinic in which specialized diagnostic equipment is available.

It is with respect to this general technical environment that aspects of the present disclosure are related.

SUMMARY

According to an embodiment of the present disclosure, there is provided a wearable device, including: a sensing module; and a strap attached to the sensing module, the wearable device being configured to be worn by a user, with a lower surface of the sensing module in contact with the user, the strap extending over an upper surface of the sensing module.

In some embodiments, the wearable device is configured to be worn on a wrist of the user.

In some embodiments, a portion of the strap is composed of an elastomer.

In some embodiments, the portion of the strap is preformed to conform to the upper surface of the sensing module and to two sides of the sensing module.

In some embodiments, a portion of the strap is a fabric band.

In some embodiments, a portion of the strap is an elastic fabric band.

In some embodiments, the strap is configured to slide longitudinally relative to the sensing module.

In some embodiments: the wearable device is configured to be worn on a wrist of the user; and the wearable device is configured to accommodate a wrist circumference of 6.8 inches.

In some embodiments: the wearable device is configured to be worn on a wrist of the user; and the wearable device is configured to accommodate a wrist circumference of 6.0 inches.

In some embodiments, the sensing module includes: a first strap slot, on a first side of the sensing module; and a second strap slot, on a second side of the sensing module, opposite the first side.

In some embodiments, the lower surface of the sensing module includes a user-contact surface.

In some embodiments, the sensing module includes: a housing having a first window in a lower surface of the housing; and a partially transparent disk, in the first window, wherein: the partially transparent disk protrudes below the lower surface of the housing, and the user-contact surface is a lower surface of the partially transparent disk.

In some embodiments, the wearable device further includes an electrical connector, wherein: the housing further has a second window in the lower surface of the housing; and the electrical connector is in the second window.

In some embodiments, the partially transparent disk is a glass-to-metal assembly including: a metal disk having a first window, and a first glass window, covering the first window of the metal disk.

In some embodiments: the first glass window does not protrude below a lower surface of the metal disk by more than 100 microns, and the first glass window is not recessed within the metal disk by more than 200 microns.

In some embodiments, a portion of the first glass window has a speckle contrast parameter of less than 0.7.

In some embodiments: the glass-to-metal assembly further includes a second glass window; the metal disk further has a second window; and the second glass window covers the second window of the metal disk.

In some embodiments: the glass-to-metal assembly has a first wall, the first wall being a portion of a partition separating a light emitting region of the sensing module from a light detecting region of the sensing module; the first window of the metal disk opens into the light emitting region; and the second window of the metal disk opens into the light detecting region.

In some embodiments, the sensing module further includes a sensor printed circuit board assembly, on the partially transparent disk, the sensor printed circuit board assembly including a spectrophotometer configured to illuminate the skin of the user with light transmitted through a first transparent portion of the partially transparent disk and to detect light returning, through a second transparent portion of the partially transparent disk, to a photodetector of the spectrophotometer after transmission through tissue of the user.

In some embodiments, the sensing module further includes: a battery carrier, on the sensor printed circuit board assembly; and a battery, on the battery carrier, wherein the battery carrier is configured to protect the battery from damage by components, of the sensing module, below the battery.

BRIEF DESCRIPTION OF THE DRAWINGS

These and other features and advantages of the present disclosure will be appreciated and understood with reference to the specification, claims, and appended drawings wherein:

DETAILED DESCRIPTION

The detailed description set forth below in connection with the appended drawings is intended as a description of exemplary embodiments of a wearable device provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Figure 1A:
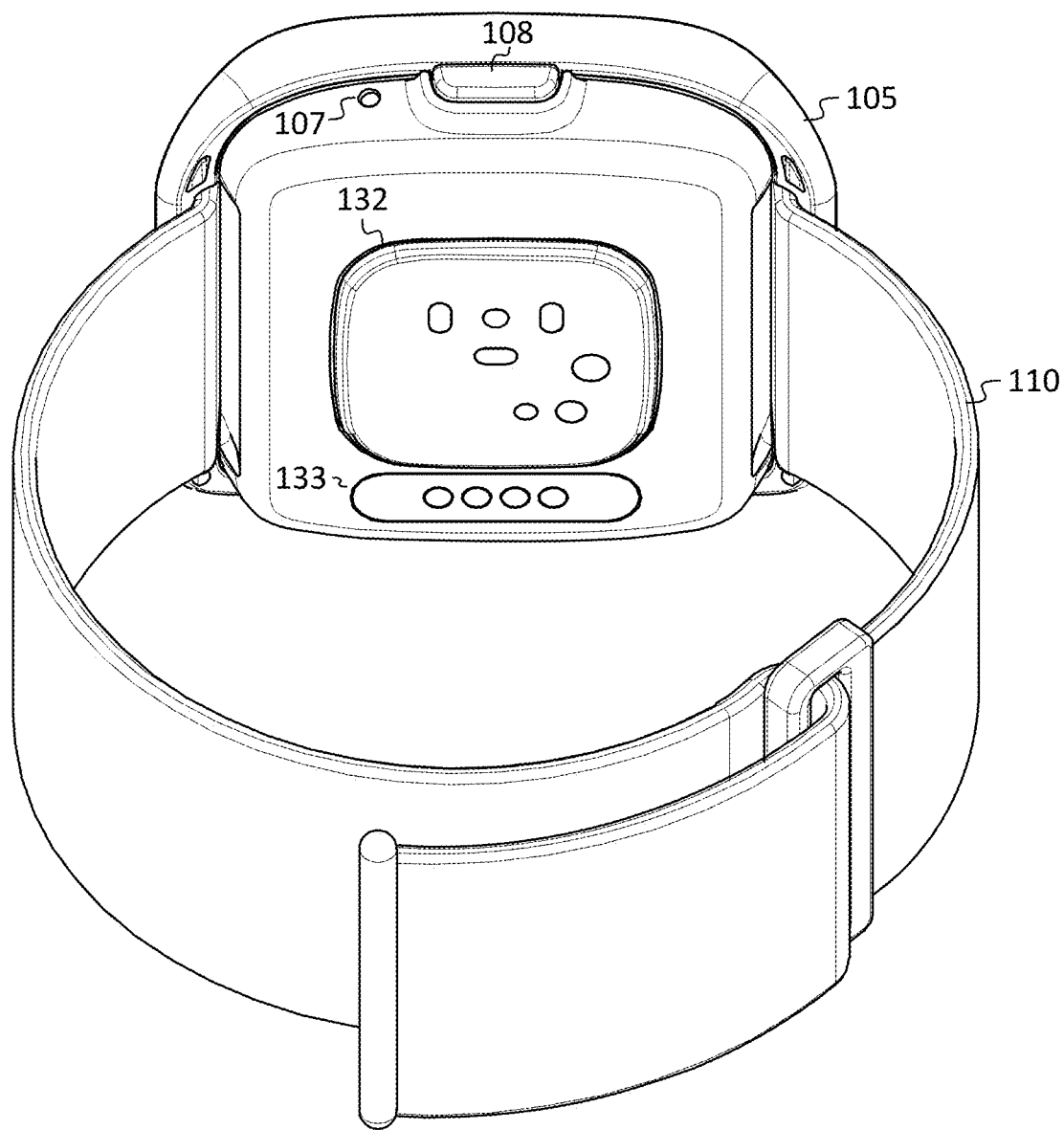
FIG. 1A is a perspective view of a wearable device, according to an embodiment of the present disclosure.

Referring to FIG. 1A, in some embodiments, a wearable device includes a sensing module 105 and a strap 110. The sensing module 105 may include a light-emitting diode (LED) indicator 107 and a button 108, as well as other features (discussed in further detail below). The wearable device may be configured to be worn by a user (e.g., on the wrist of the user, or with a suitably sized band, elsewhere on the user, e.g., on the leg or chest of the user, as discussed in further detail below). The lower surface of the sensing module 105 may include a partially transparent disk (e.g., a glass-to-metal assembly 132, as illustrated) the lower surface of which may be a user contact surface which, when the wearable device is worn by a user, is in contact with the skin of the user. As used herein, a "partially transparent disk" is a disk having transparent portions and opaque portions. In the embodiment of FIG. 1A, the partially transparent disk includes seven transparent portions, each of which may be a glass window covering a respective opening (or "window") in a metal disk having seven windows. As used herein, a "window" is either (i) an opening, or (ii) a transparent or translucent element covering such an opening, or (iii) a clear portion of an otherwise opaque sheet. The sensing module 105 may include one or more sensors configured to interact optically, through the windows, with the tissue of a user, as discussed in further detail below. The lower surface of the sensing module 105 may further include an electrical connector, or "charge port" 133 which may be used to charge the sensing module 105, or to communicate with the sensing module 105.

Figure 1B:
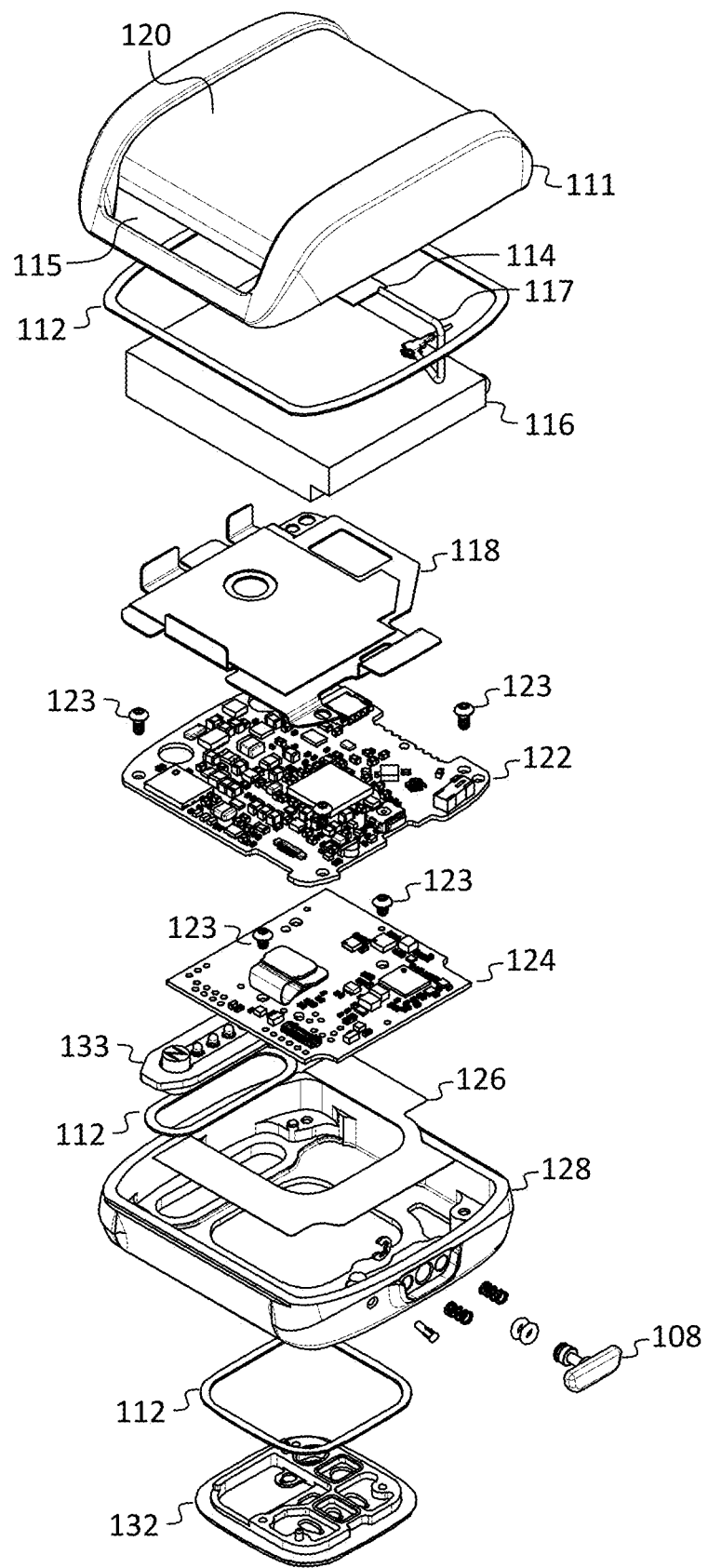
FIG. 1B is an exploded perspective view of a sensing module, according to an embodiment of the present disclosure.

Referring to FIG. 1B, the sensing module 105 may include a housing including an upper housing, or "cover" 111 (which may be composed of a polymer, e.g., injection molded plastic), a lower housing, or "caseback" 128 (which may be composed of metal, e.g., stainless steel), and the partially transparent disk 132. The strap 110 may be attached to the sensing module, e.g., the strap 110 may extend through a first strap slot 115 on a first side of the upper housing 111, over an upper surface of the sensing module (in a channel 120 in the top of the upper housing 111), and through a second strap slot on a second side (opposite the first side) of the upper housing 111. The sensing module 105 may further include, within the housing, an insulating sheet 126 (e.g., a Kapton sheet) on the inner lower surface of the lower housing 128, a sensor printed circuit board assembly (PCBA) 124 (secured in place by screws 123) on the insulating sheet, a host printed circuit board assembly 122 (secured in place by screws 123) on the sensor printed circuit board assembly 124, a battery carrier 118 on the host printed circuit board assembly 122, a battery 116 (e.g., a lithium polymer (LiPo) battery) on the battery carrier 118, and an antenna 114 (connected to the host printed circuit board assembly by a coaxial cable 117) on the battery 116. The battery carrier 118 may be or include a rigid (e.g., metal) sheet to protect the battery 116 from damage by components on the host printed circuit board assembly 122 (e.g., to protect the battery 116 from being punctured by, e.g., components with sharp corners). In some embodiments the lower housing 128 is composed of a dielectric material (e.g., injection molded plastic) and the insulating sheet 126 may be absent. The upper housing 111 may be secured to the lower housing 128 by pressure-sensitive adhesive 112 (or, if the lower housing 128 is composed of injection molded plastic, by ultrasonic welding).

Figure 1C:
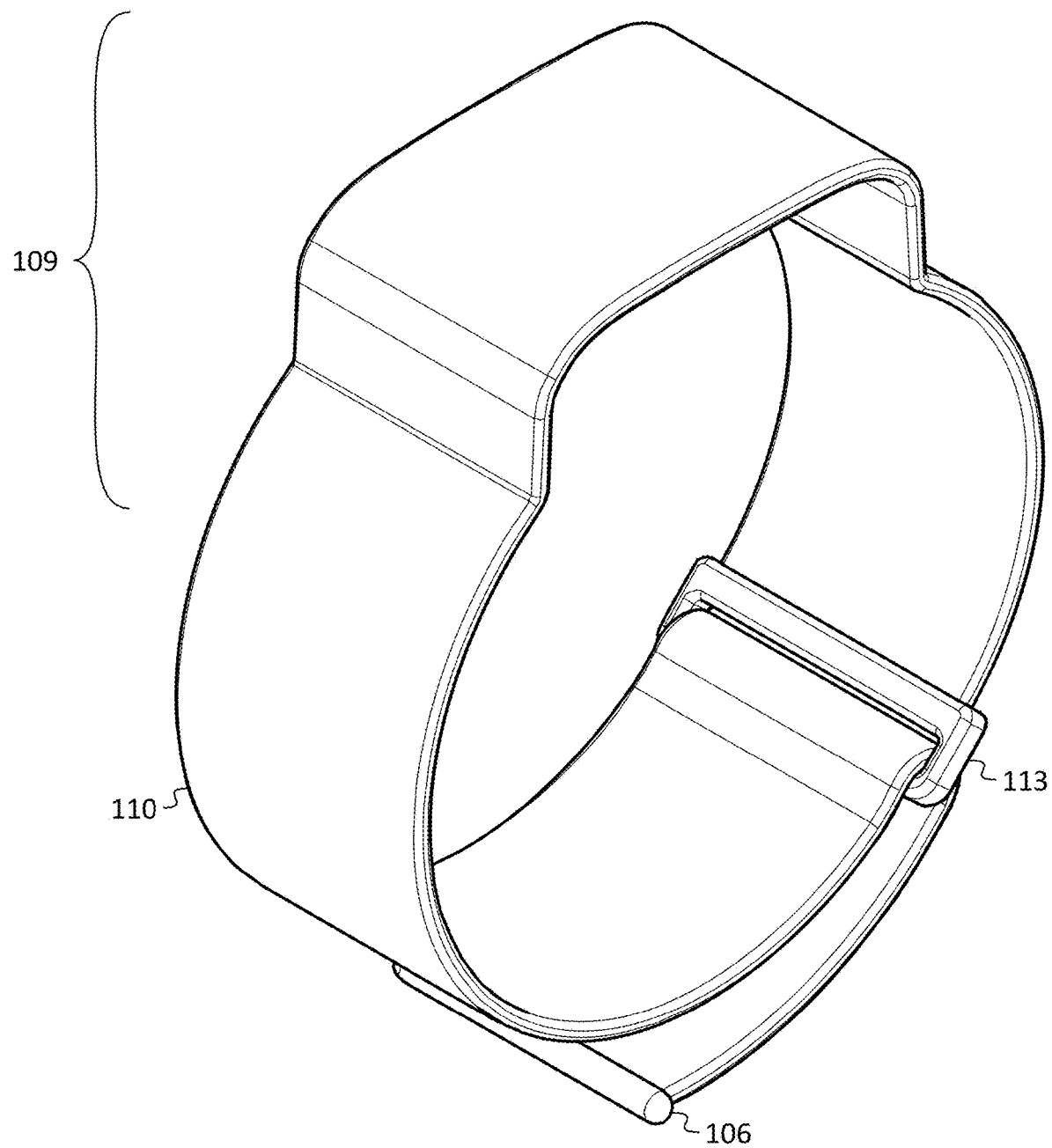
FIG. 1C is a perspective view of a strap, according to an embodiment of the present disclosure.

Referring to FIG. 1C, the strap 110 may be composed of an elastomer, a portion (e.g., an upper portion 109) of which may be pre-formed to conform to the upper surface of the sensing module (e.g., to the upper surface of the upper housing 111). As used herein, the strap 110 being "preformed" to conform to the upper surface means that the strap 110 is fabricated such that when no external force is applied to the strap 110 to deform it, it assumes a shape (such as that shown in FIG. 1C) a portion 109 of which is the shape a strap 110 has if fed through the first strap slot 115, through the channel 120, and through the second strap slot. The strap 110 may have two ends and a clasp (e.g., an adjustable clasp) for securing the two ends together. In some embodiments, the strap 110 is a fabric band that is capable of sliding longitudinally within the strap slots 115 and the channel 120, to provide an increased range of adjustability, so that an increased range of wrist sizes may be accommodated. In some embodiments, the strap 110 has a loop 113 at one end and the second end is configured to pass through the loop and fold back on itself, as illustrated in FIGS. 1A and 1C. An end cap 106 may prevent the end of the strap from slipping out of the loop 113, facilitating the one-handed fitting of the band to a user's wrist, by the user's other hand. In some embodiments, the strap 110 is able to accommodate (e.g., fit snugly on) a minimum wrist circumference between 4.5 inches and 7.0 inches. In some embodiments, the strap 110 is able to accommodate (e.g., fit on) a maximum wrist circumference of between 6.0 inches and 8.5 inches. In some embodiments, the strap 110 is an elastic fabric band.

Figure 1D:
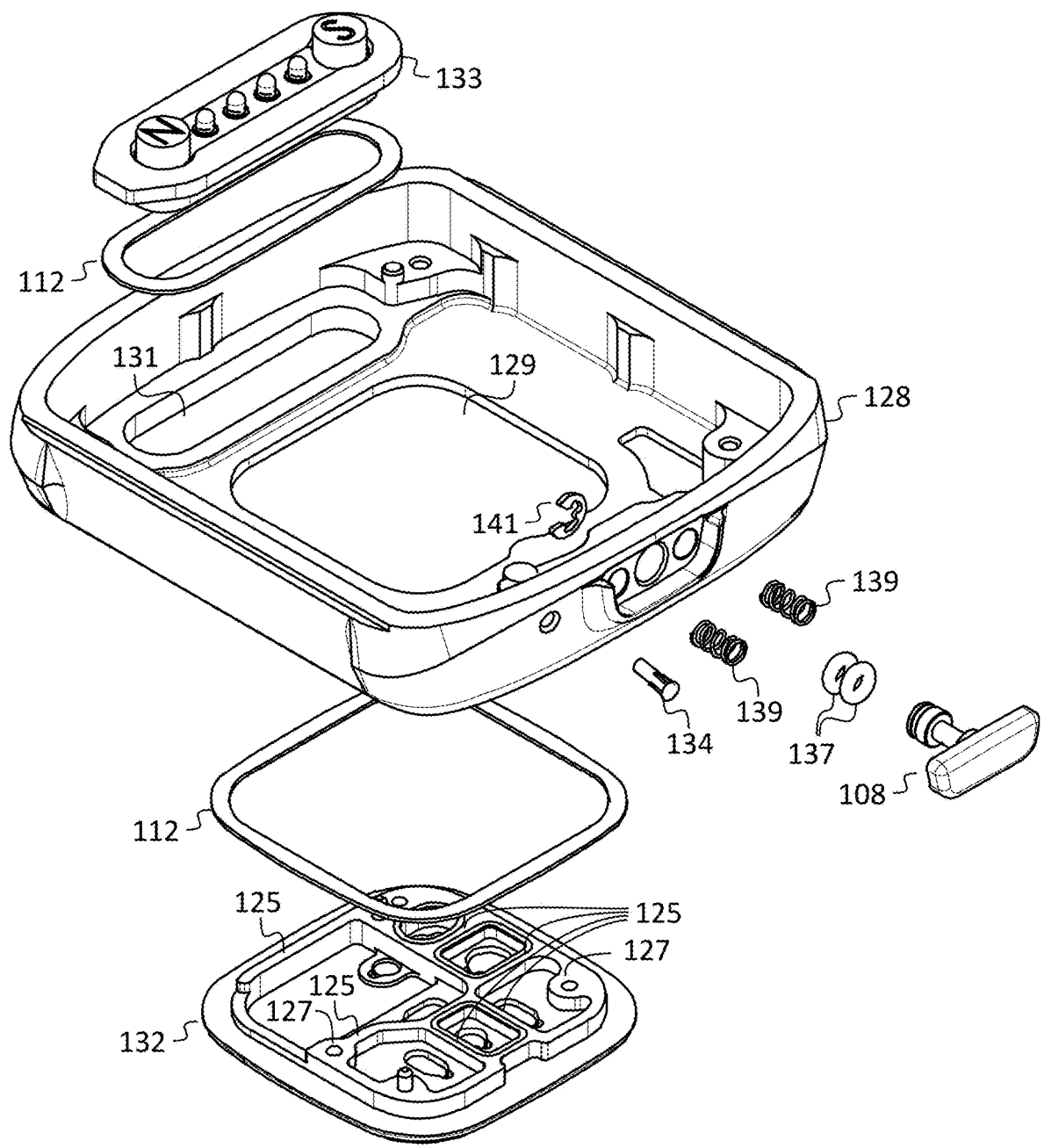
FIG. 1D is an exploded perspective view of a portion of a sensing module, according to an embodiment of the present disclosure.

Referring to FIG. 1D, the lower housing 128 may include (i) a first window 129 into which the partially transparent disk 132 may fit, and to which the partially transparent disk 132 may be secured and sealed with a pressure-sensitive adhesive (PSA) 112, and (ii) a second window 131 into which the electrical connector 133 may fit and to which the electrical connector 133 may be secured and sealed with a pressure-sensitive adhesive 112. In some embodiments the lower housing 128 is composed of plastic (and may be formed by injection molding); in such an embodiment the second window 131 may be absent and the conductors of the electrical connector 133 may be insert-molded directly into the lower housing 128.

Figure 1E:
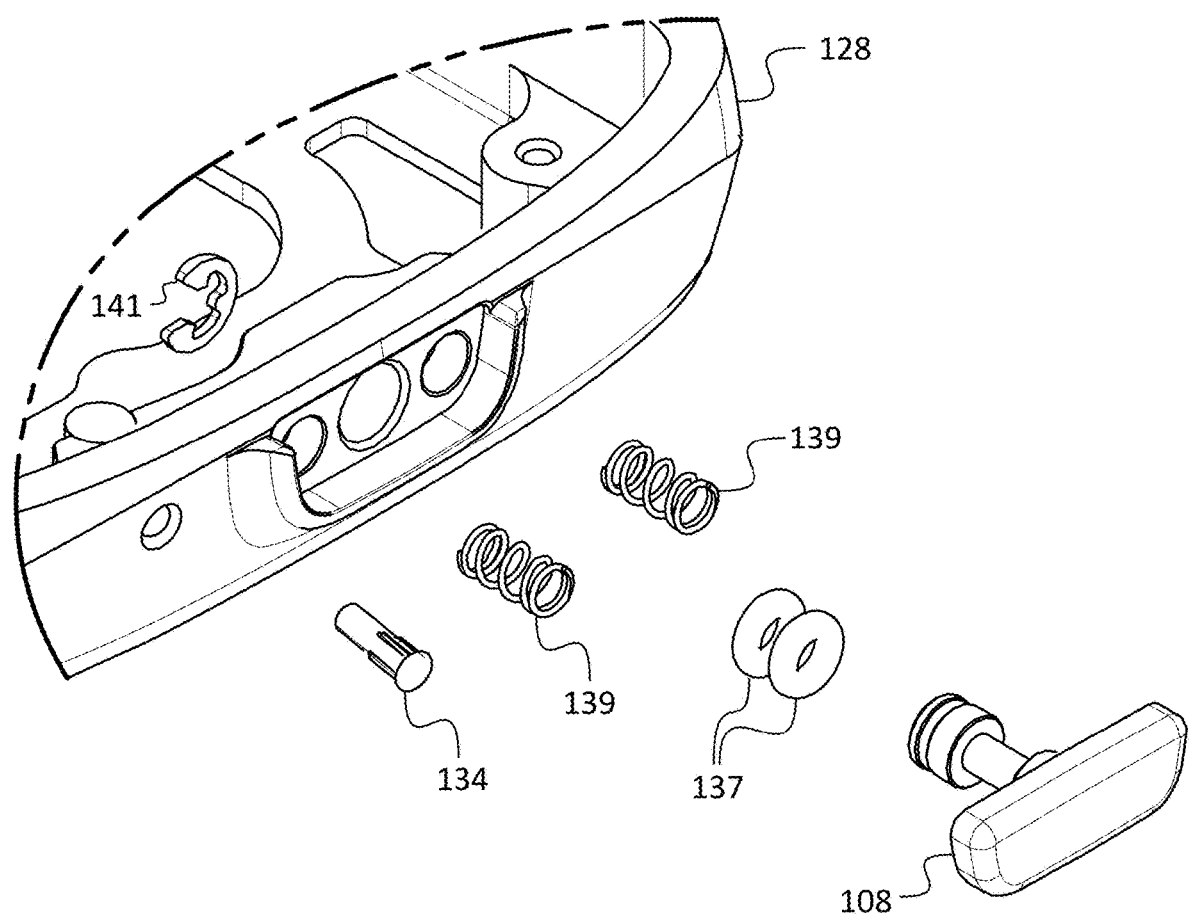
FIG. 1E is an exploded perspective view of a portion of a sensing module, according to an embodiment of the present disclosure.

The button 108 may seal against the lower housing 128 with two O-rings 137. Two springs 139 may return the button 108 to its home position after being pressed, and it may be prevented from extending too far out of the lower housing 128 by an E-clip 141. The LED indicator 107 may include a light pipe 134, which guides light from an LED 136 (FIG. 1K) through the wall of the lower housing 128. The partially transparent disk 132 (e.g., the glass-to-metal assembly) may have a plurality of screw bosses 127 each for receiving a respective screw 123. The partially transparent disk 132 may further have one or more walls 125 each of which is a portion of a partition separating a light emitting region of the sensing module from a light detecting region of the sensing module. Each of these regions may be a volume in the sensing module 105 that is, except for a window, optically sealed. For example (as discussed in further detail below), light blocking epoxy may be dispensed onto the top surface of each wall 125, and an opaque cover (e.g., a printed circuit board assembly) may be placed over the tops of the walls 125, to seal each region. Sealing the light emitting regions off from the light detecting regions may reduce noise and sensing errors that otherwise may be associated with leakage of light from a light emitting region into a light detecting region. The glass-to-metal assembly 132 may be formed by bonding a glass window over each of a plurality of windows (openings) of a metal disk. The metal disk may be fabricated by computer numerically controlled (CNC) machining or by metal injection molding. The glass windows may be bonded to the metal disk using epoxy, or using a hermetic metal-to-glass seal. Each glass window may have a lower surface flush with, or slightly recessed within, the lower surface of the metal disk, so that (i) the lower surface of the glass window may be in contact with the skin of the user (and there is no air gap between the glass and skin) and (ii) the lower surface of the metal disk may be in contact with the skin of the user (avoiding the presence of an air gap, through which light may leak, between the metal disk and the skin of the user). For example, in some embodiments, the first glass window does not protrude below a lower surface of the metal disk by more than 100 microns, and the first glass window is not recessed within the metal disk by more than 200 microns. FIG. 1E is an enlarged view of a portion of FIG. 1D.

Figure 1F:
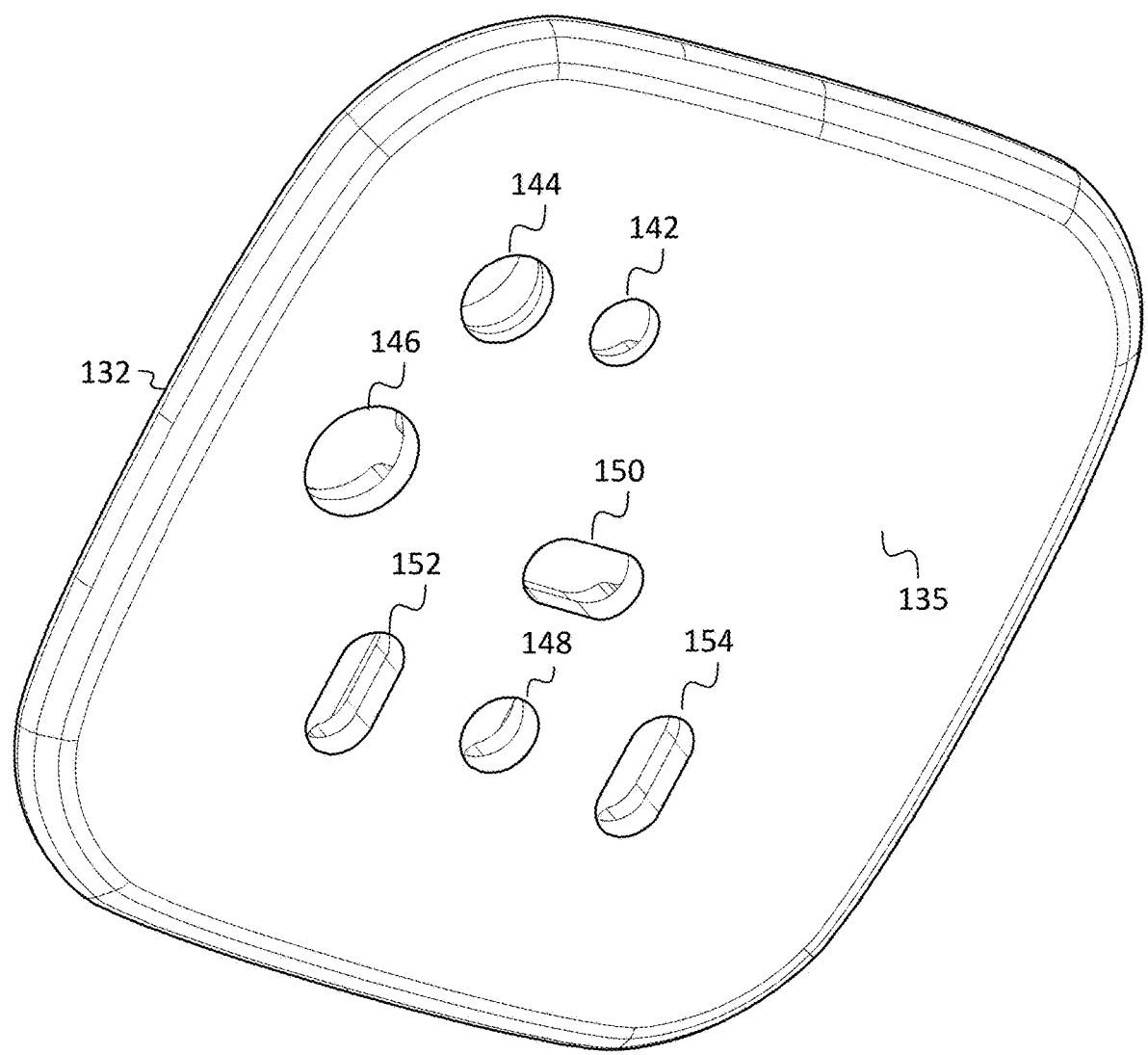
FIG. 1F is a perspective view of a portion of a sensing module, according to an embodiment of the present disclosure.

The sensing module may include a laser light source, and a plurality of light-emitting diode (LED) light sources. FIG. 1F shows a user-contact surface 135 of the glass-to-metal assembly 132 of FIGS. 1A, 1B and 1D. In some embodiments, the partially transparent disk 132 protrudes below the exterior lower surface of the housing (e.g., by between 1.0 mm and 4.0 mm), to provide improved contact between the user-contact surface 135 and the skin of the user. The laser light source, which may illuminate the skin of the user through a first glass window 142, may include an array of short wave infrared (SWIR) lasers each operating at a different respective wavelength; these lasers may be turned on one at a time. A first detector, behind a second glass window 144, may receive the laser light after it has been transmitted through tissue of the user (e.g., through the skin or through the skin and through tissues beneath the skin). The wavelength dependence of the fraction of the transmitted light detected by the detector may be employed to infer aspects of the chemical composition of the tissue. Such a device, which measures the transmission (e.g., through tissue of a user) at two or more wavelengths, may be referred to herein as a "spectrophotometer". A red LED and an infrared LED (which may be co-packaged) may illuminate the skin of the user through a third glass window 146, and a green LED may illuminate the skin of the user through a fourth glass window 148. Three detectors, behind respective glass windows (a fifth glass window 150, a sixth glass window 152, and a seventh glass window 154) may each receive the light from one or more of the LEDs after it has been transmitted through tissue of the user. In some embodiments, e.g., ones in which the sensing module 105 comprises two independent sensing systems (e.g., one using a laser light source and one using an LED) that do not operate simultaneously, the light emitting region of one sensing system may share a region or compartment with a light detecting region of another sensing system. The interior surface of either or both of the first glass window 142 and the second glass window 144 may roughened (e.g., by laser etching or sand blasting) to have a transmission of at least 60% (e.g., at least 85%), a scatter fraction of at least 70% (e.g., at least 95%), and a speckle contrast parameter of less than (e.g., a speckle contrast parameter of less than 0.55). Such a surface may have a surface roughness with an average of profile height deviations from the mean line (Ra) of microns. Roughening of the transmitting window may improve illumination uniformity and device to device variability and roughening of the receiving window may reduce Fresnel reflection and bring the speckle generating surface closer to the detector, providing speckle noise mitigation.

In some embodiments, aluminum oxynitride windows may be used instead of glass windows. Such aluminum oxynitride windows may be fabricated by loading aluminum oxynitride powder into cavities in the metal disk, and placing the metal disk, together with a suitable mold, into a hot isostatic press (HIP), with surfaces of the mold defining the surfaces of the aluminum oxynitride that are not in direct contact with the metal disk. Because the aluminum oxynitride windows are being produced from a mold, the aluminum oxynitride windows may be manufactured as lenses, or they may be molded to have a shape that is close to a desired final shape, making it easier to then achieve the final desired shape.

Figure 1G:
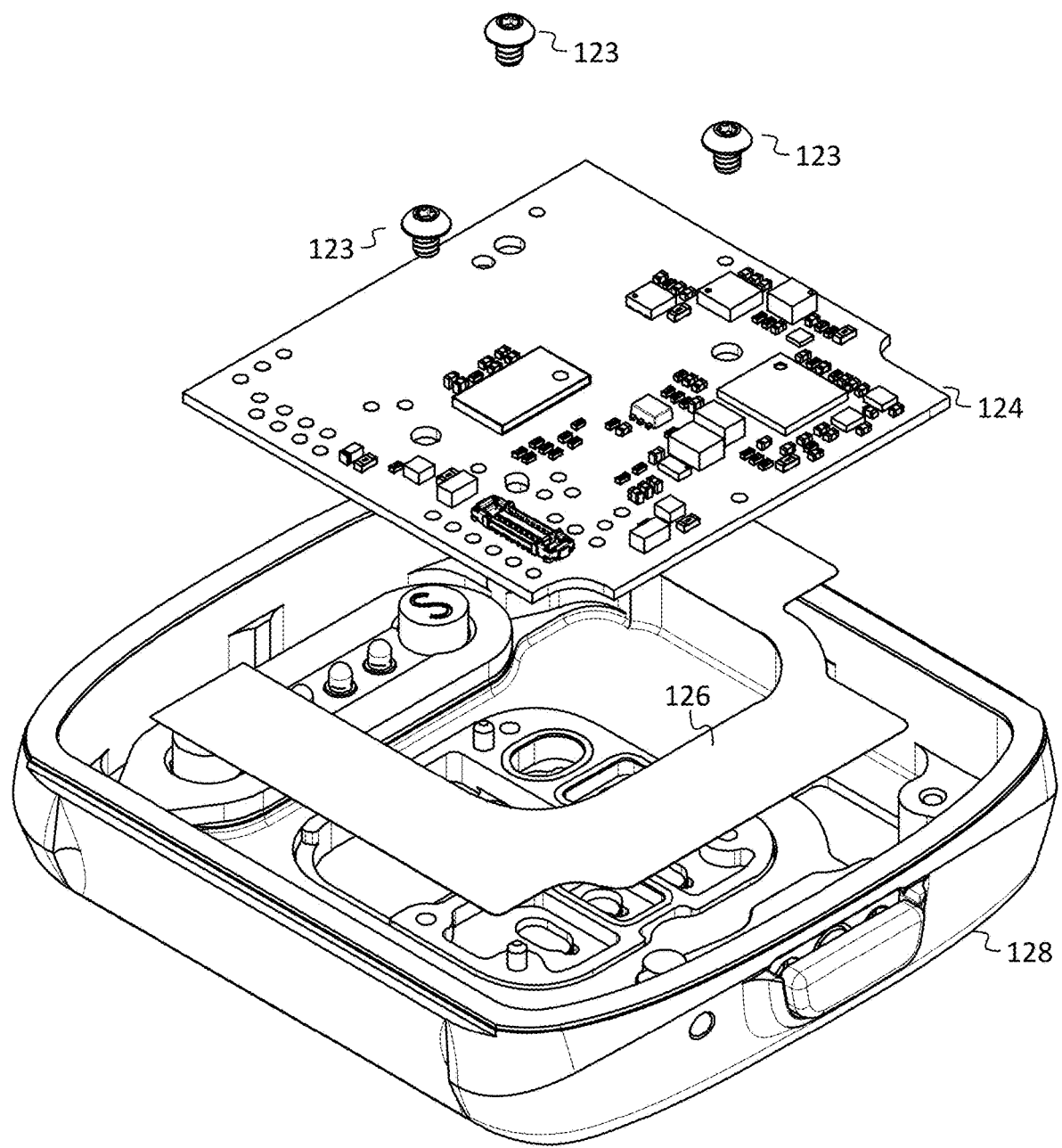
FIG. 1G is an exploded perspective view of a portion of a sensing module, according to an embodiment of the present disclosure.
Figure 1H:
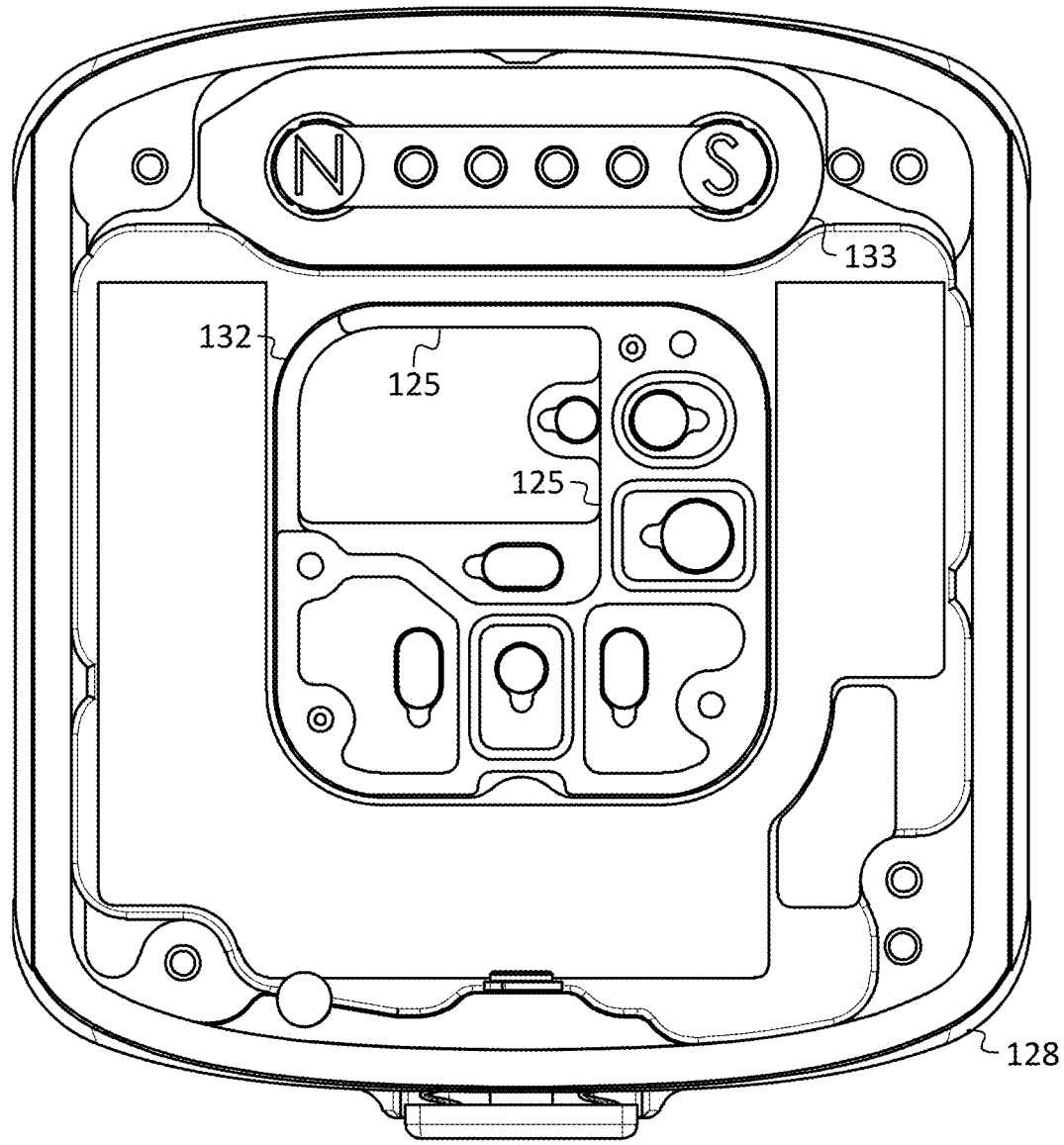
FIG. 1H is a plan view of a portion of a sensing module, according to an embodiment of the present disclosure.
Figure 1I:
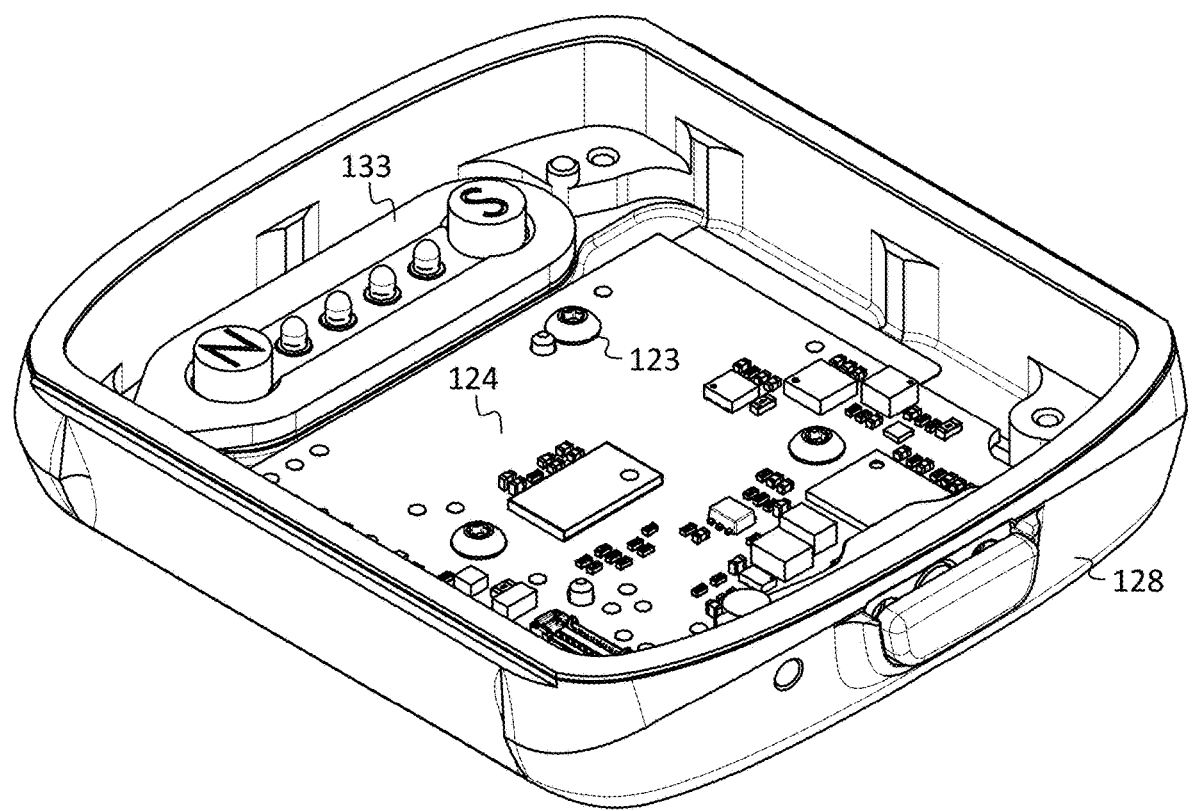
FIG. 1I is a perspective view of a portion of a sensing module, according to an embodiment of the present disclosure.
Figure 1J:
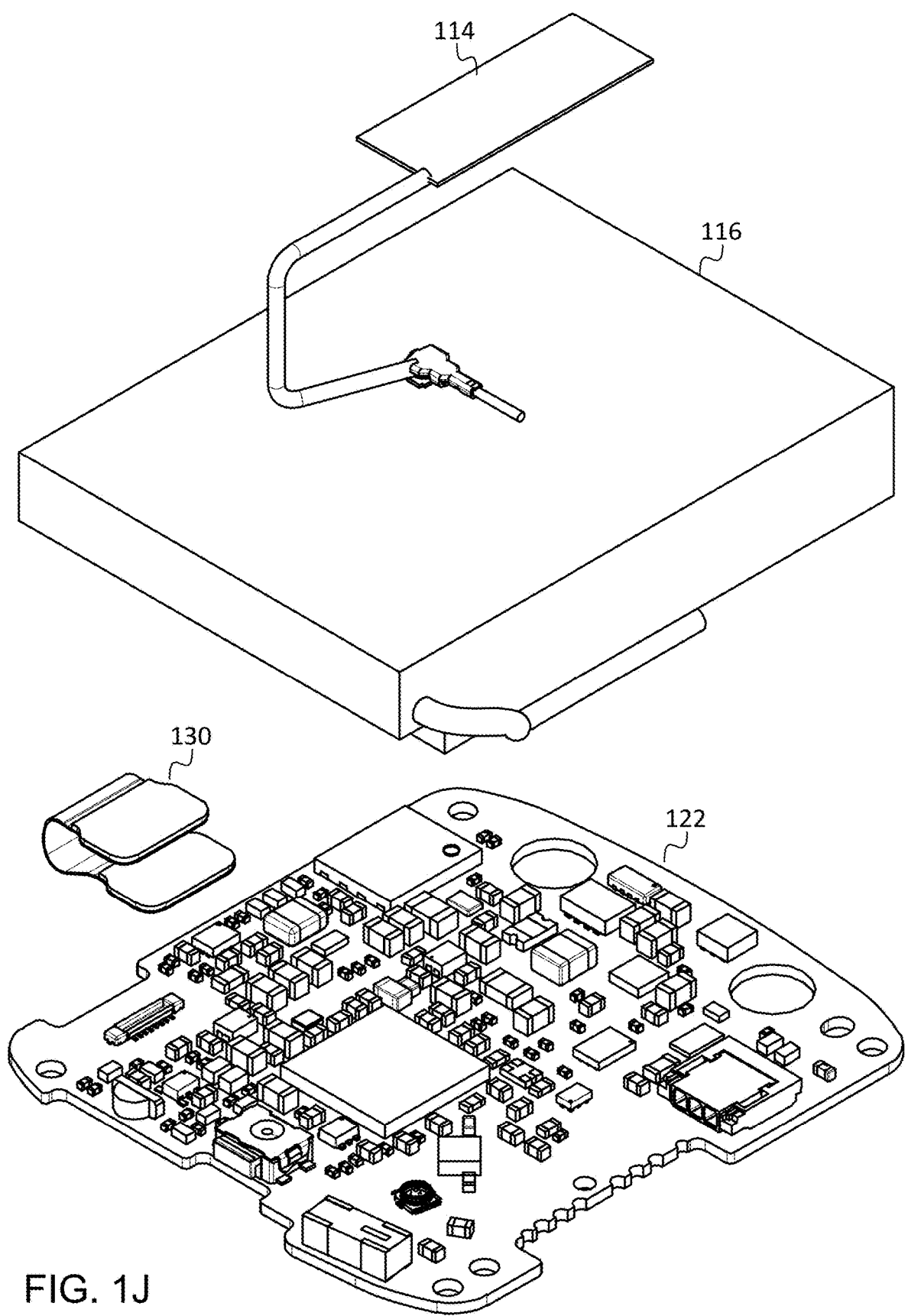
FIG. 1J is an exploded perspective view of a portion of a sensing module, according to an embodiment of the present disclosure.
Figure 1K:
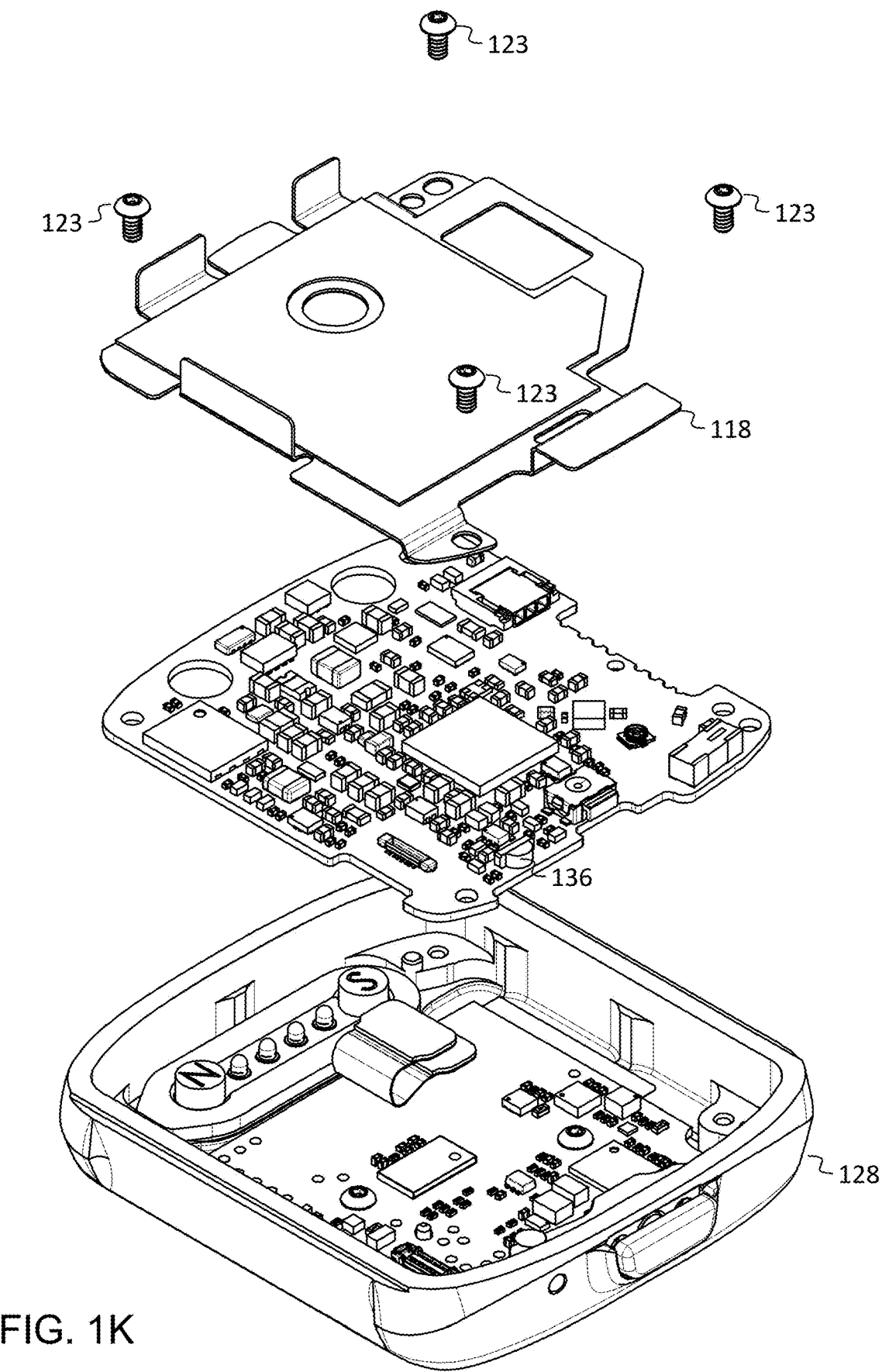
FIG. 1K is an exploded perspective view of a portion of a sensing module, according to an embodiment of the present disclosure.
Figure 2A:
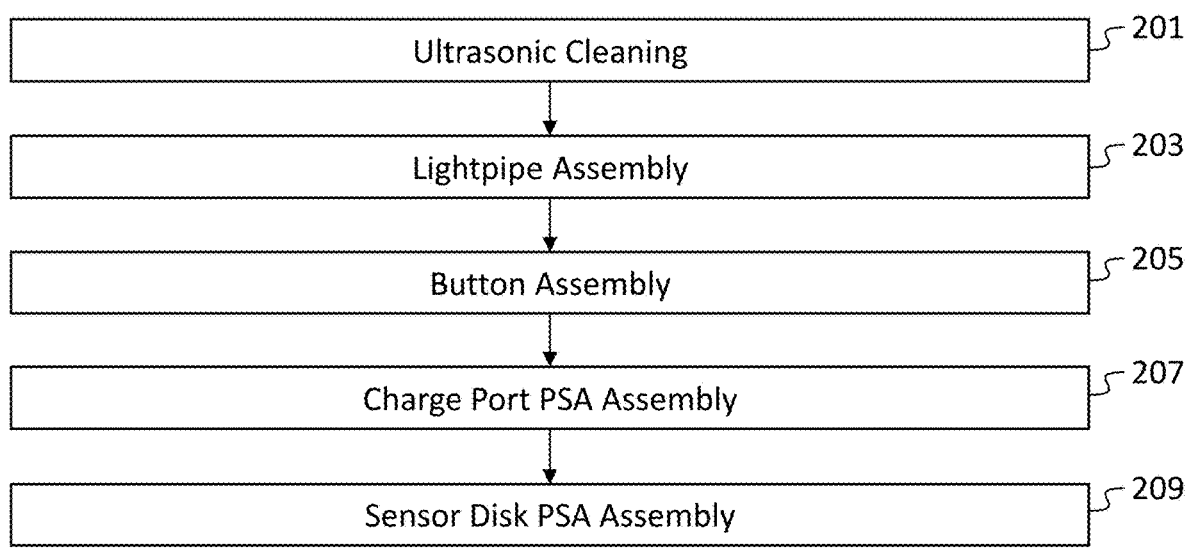
FIG. 2A is a flowchart of a method, according to an embodiment of the present disclosure.
Figure 2B:
FIG. 2B is a flowchart of a method, according to an embodiment of the present disclosure.
Figure 2C:
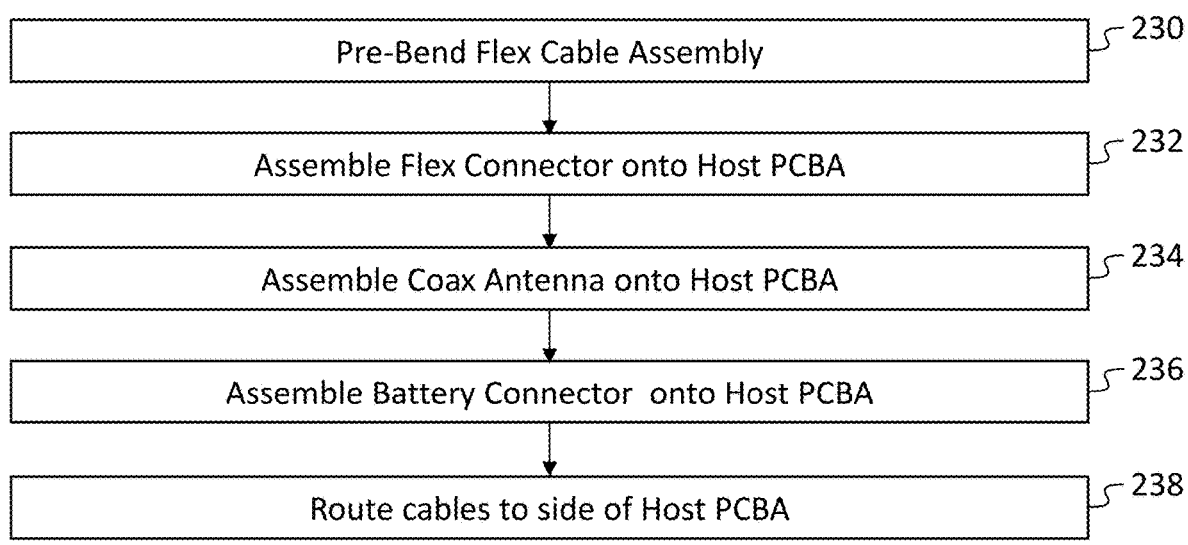
FIG. 2C is a flowchart of a method, according to an embodiment of the present disclosure.

FIG. 2A shows a method (corresponding to FIGS. 1D and 1E) that may be employed to assemble the lower housing 128 with certain other components. The method includes ultrasonic cleaning at 201, installation of the light pipe assembly at 203, installation of the button assembly at 205, installation of the charge port, using the charge port PSA 112, at 207, and installation of the sensor disk (the glass-to-metal assembly 132), using a respective PSA 112, at 209. FIG. 2B shows a flowchart of a method (corresponding to FIGS. 1G, 1H, and 1I) for installing the sensor printed circuit board assembly 124 in the lower housing 128. The method includes placing the caseback 128 in a fixture or tray at 212, placing the insulating sheet 126 (e.g., the Kapton tape) at 214, dispensing light blocking epoxy at 216, applying thread lock to screw bosses 127 (in three places) at 218, placing the sensor PCBA 124 at 220, torquing the three screws at 222, flipping the parts in the fixture or tray at 224, applying a heat cure at 226, and performing, at 228, an optical test and a hardware (HW) built-in self-test (BIST). In the embodiment of FIG. 2B, the sensor printed circuit board assembly 124, which is optically sealed to the tops of walls 125 of the glass-to-metal assembly 132, operates as the opaque cover for the glass-to-metal assembly 132. To increase the opacity of the sensor printed circuit board assembly, the ground planes of the sensor printed circuit board assembly may be filled as much as possible (e.g., each ground plane may be at least 30% filled), and black solder mask may be used. FIG. 2C shows a flowchart of a method (corresponding to FIG. 1J) for assembling the host printed circuit board assembly 122, the battery 116, and the antenna 114. The method includes pre-bending the flex cable assembly 130 at 230, assembling the flex cable assembly 130 onto the host PCBA 122 at 232, assembling the coax antenna 114 onto the host PCBA 122 at 234, assembling the battery connector onto the host PCBA 122 at 236, and routing cables, at 238, (e.g., the coaxial cable of the coax antenna 114 and wiring for the battery) to the side of the host PCBA 122.

Figure 1L:
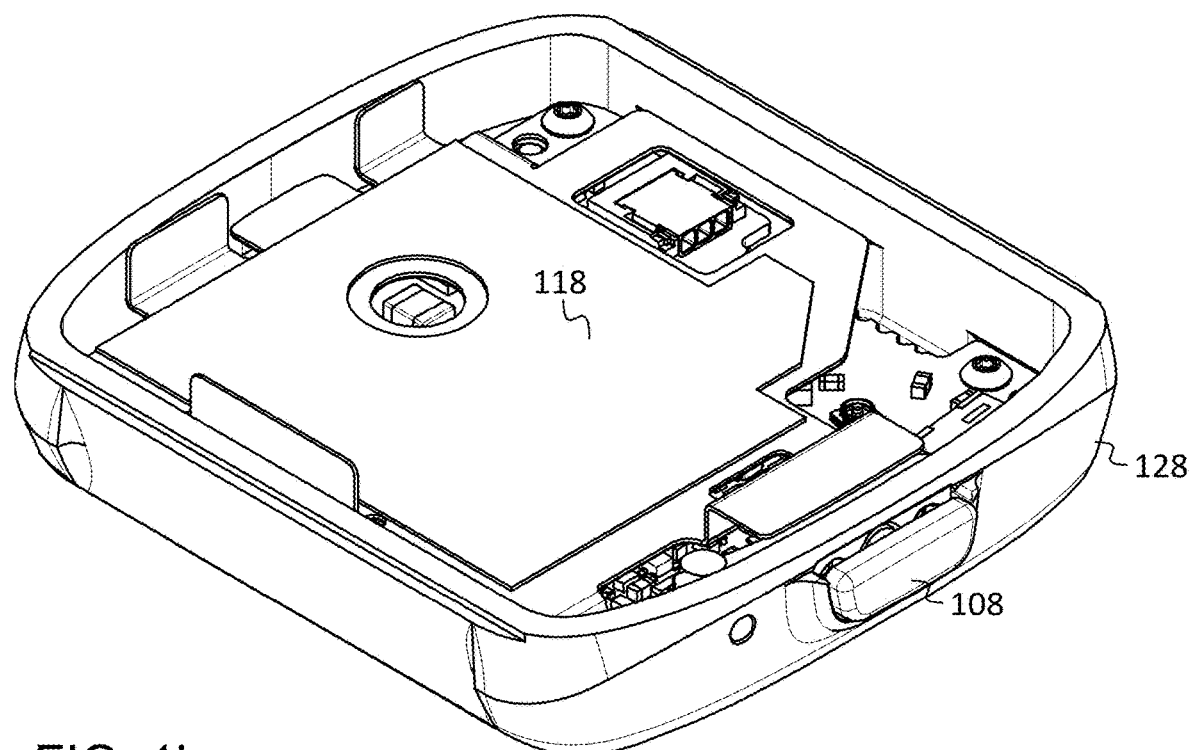
FIG. 1L is a perspective view of a portion of a sensing module, according to an embodiment of the present disclosure.
Figure 1M:
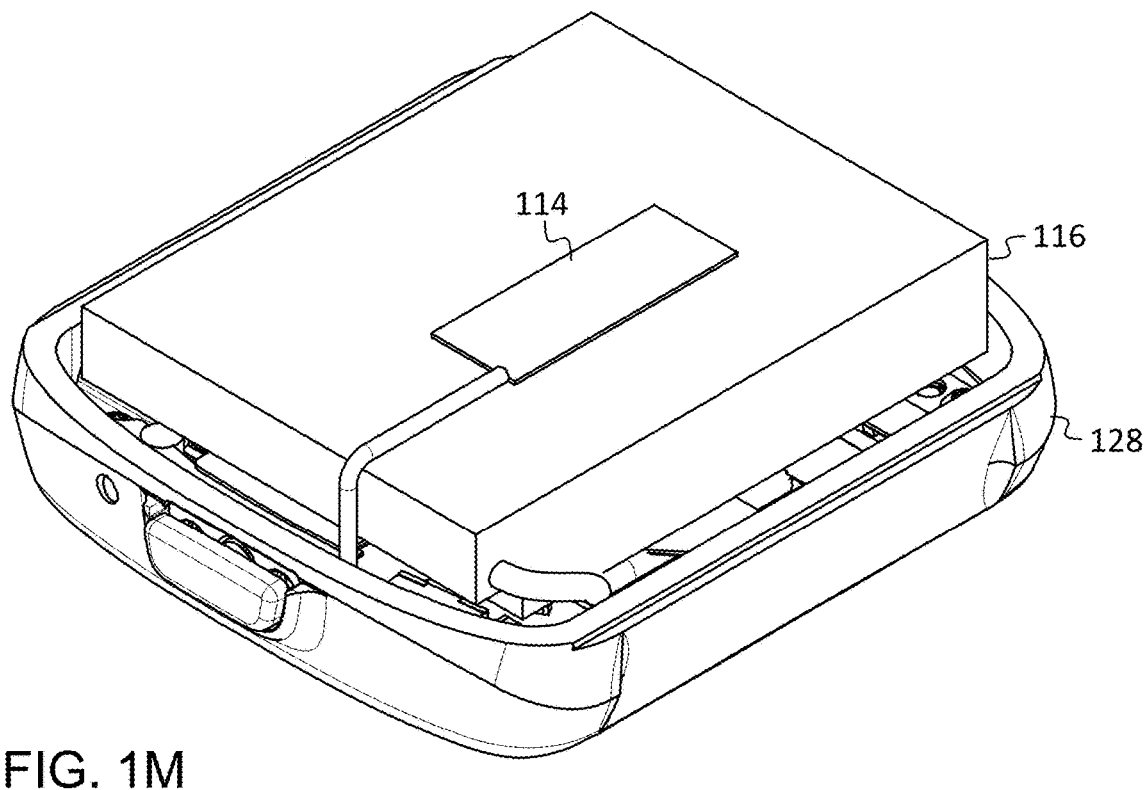
FIG. 1M is a perspective view of a portion of a sensing module, according to an embodiment of the present disclosure.
Figure 2D:
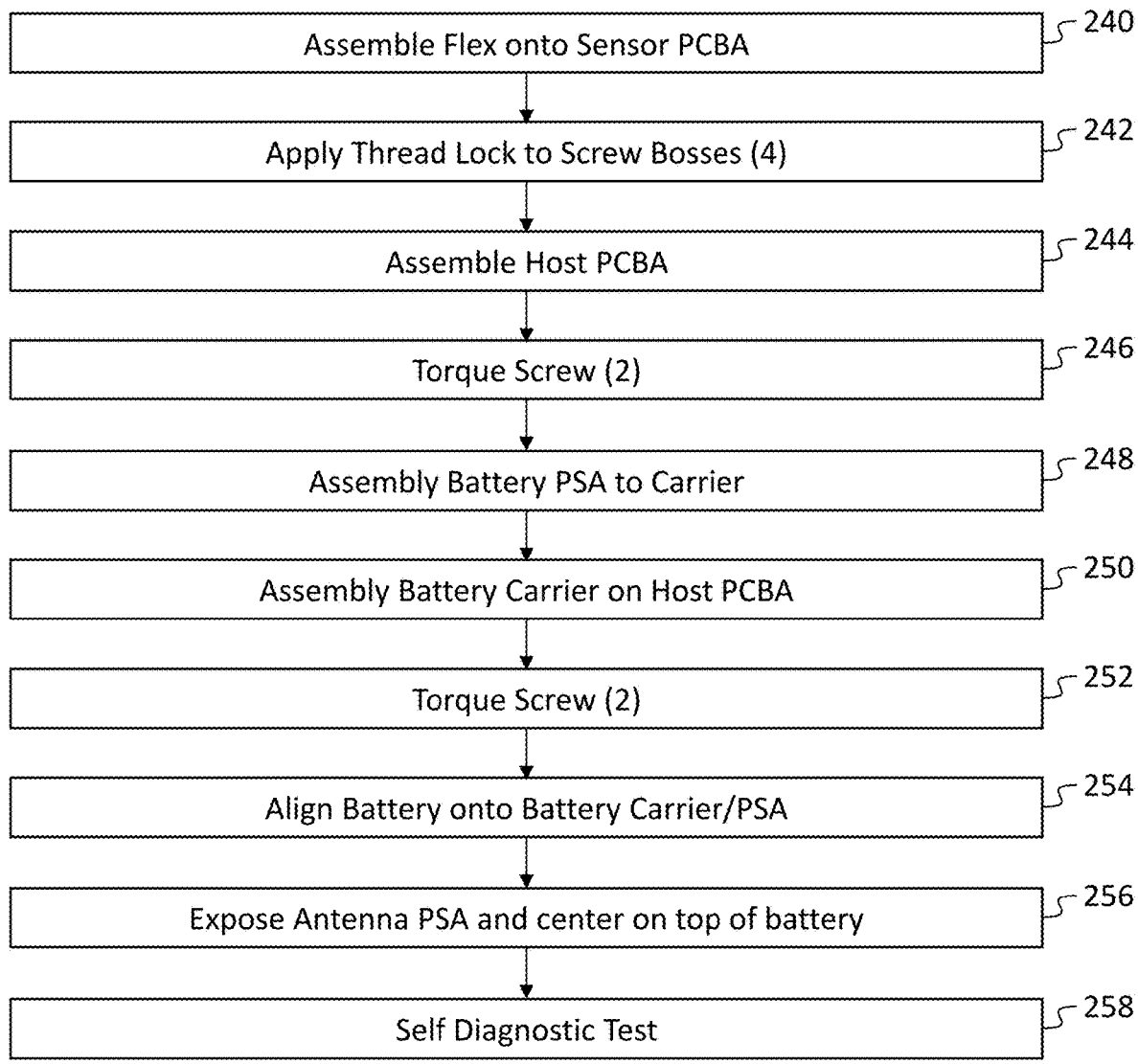
FIG. 2D is a flowchart of a method, according to an embodiment of the present disclosure.

FIG. 2D is a flowchart of a method (corresponding to FIGS. 1K, 1L, and 1M), in some embodiments. The method includes assembling the flex cable 130 onto the sensor PCBA 124 at 240, applying thread lock to screw bosses 127 in four places at 242, assembling the host PCBA 122 at 244, torquing two screws 123 at 246, assembling the battery PSA 112 to the battery carrier 118 at 248, assembling the battery carrier 118 on the host PCBA 122 at 250, torquing two screws 123 at 252, aligning the battery 116 onto the battery carrier 118 and the PSA 112 at 254, exposing the antenna PSA 112 and centering it on top of the battery 116 at 256, and performing a self-diagnostic test at 258.

Figure 1N:
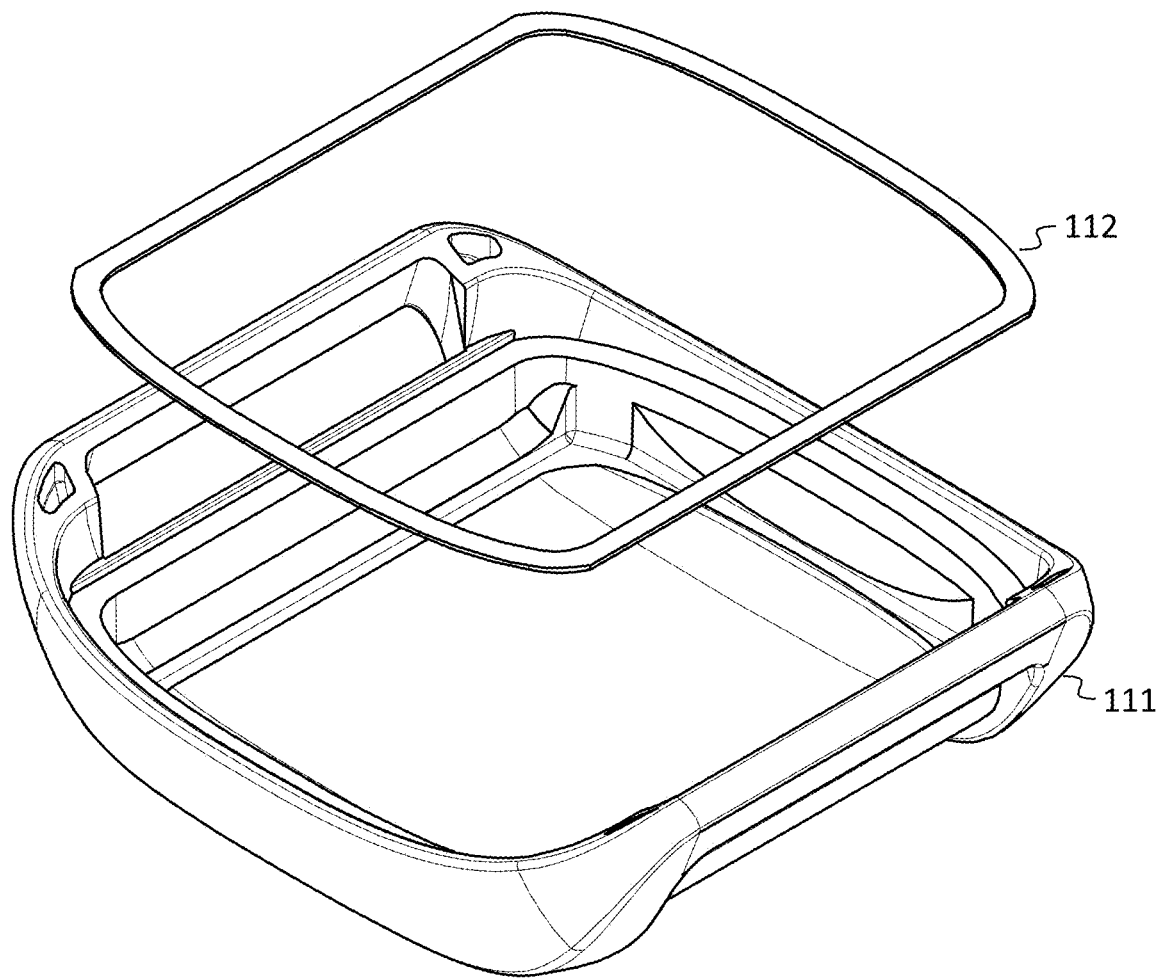
FIG. 1N is an exploded perspective view of a portion of a sensing module, according to an embodiment of the present disclosure.
Figure 1O:
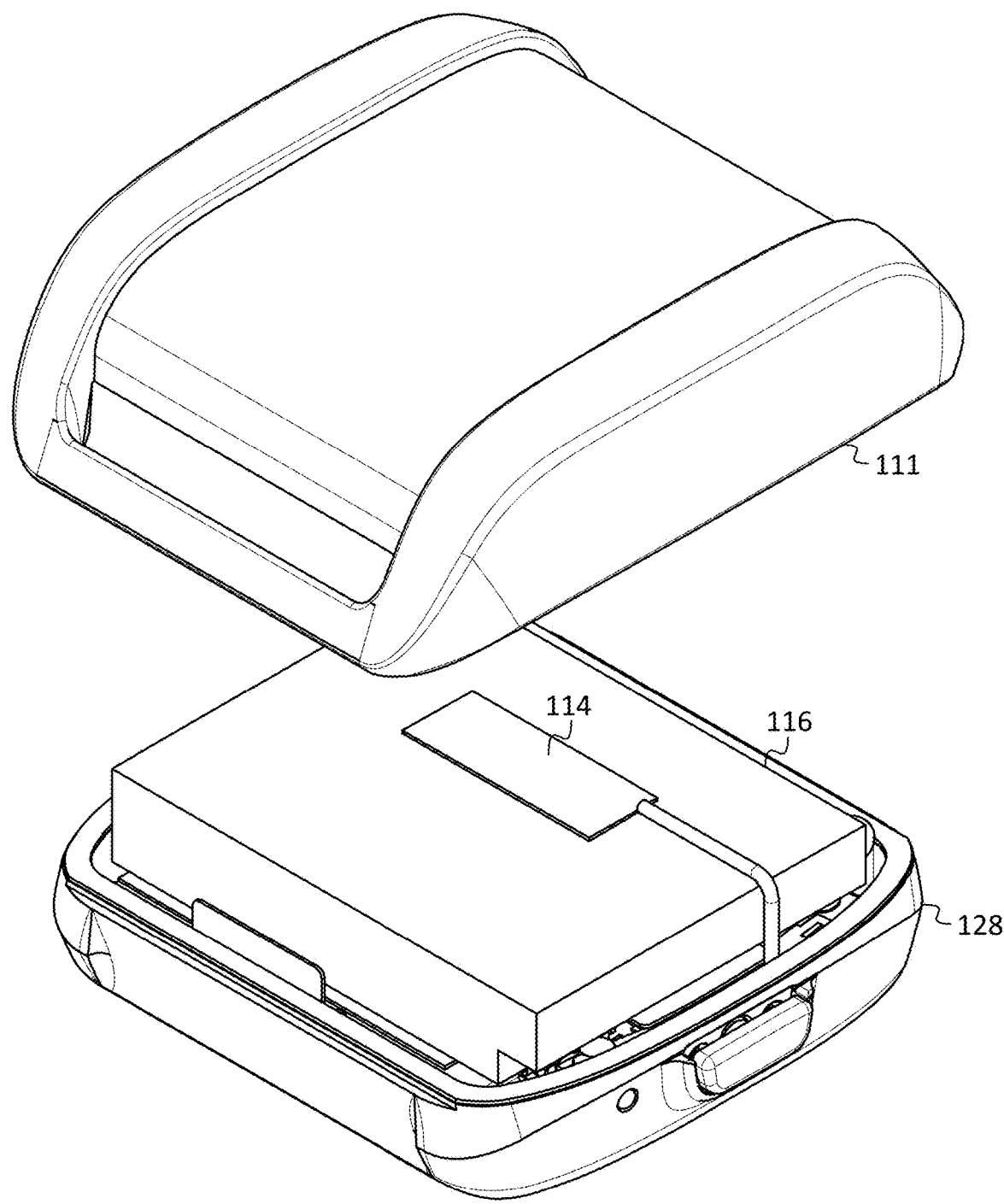
FIG. 1O is an exploded perspective view of a sensing module, according to an embodiment of the present disclosure.
Figure 2E:
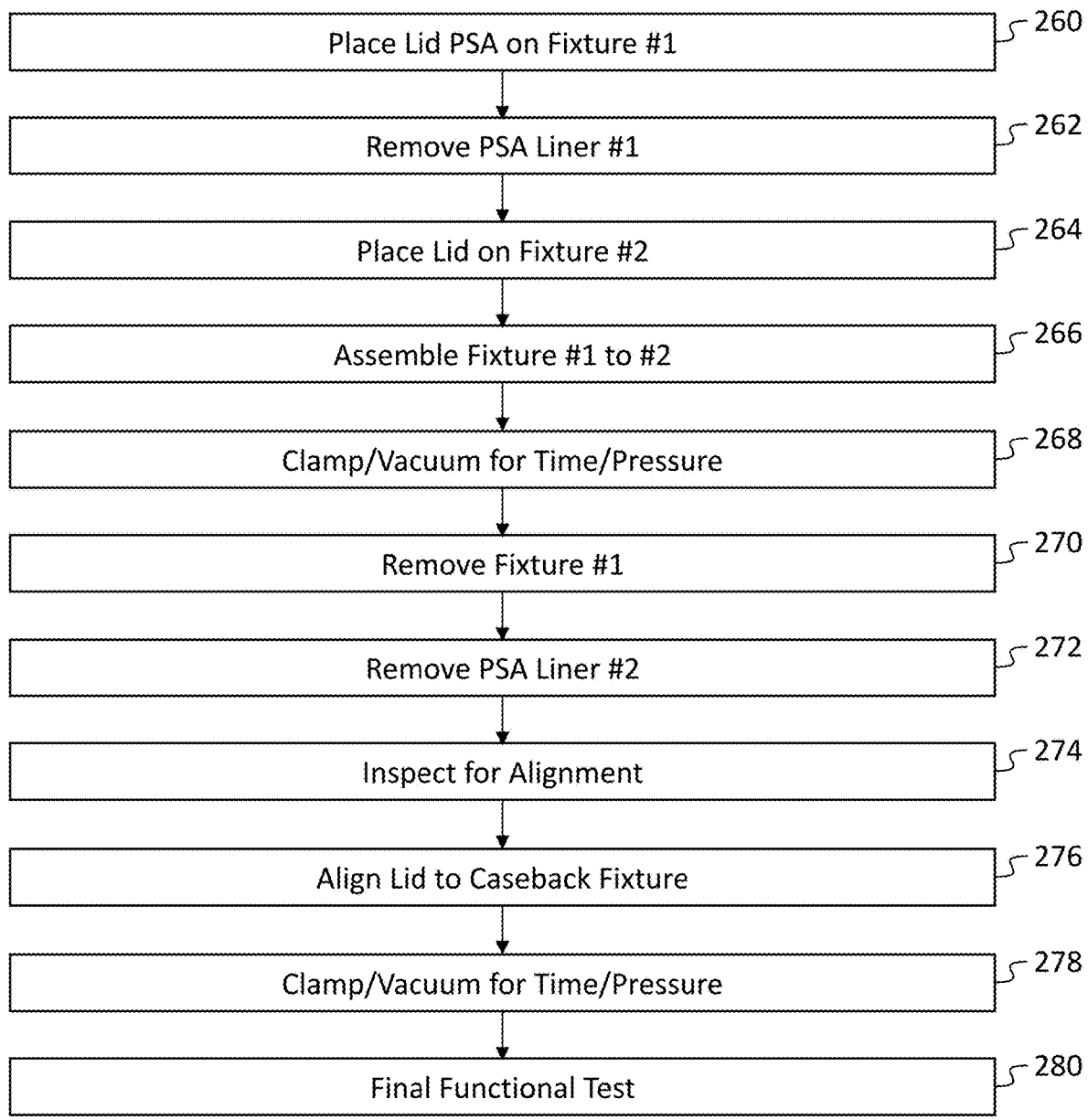
FIG. 2E is a flowchart of a method, according to an embodiment of the present disclosure.

FIG. 2E is a flowchart of a method (corresponding to FIGS. 1N and 1O), in some embodiments. The method includes placing the lid PSA 112 on a fixture (which may be referred to as Fixture #1) at 260, removing a PSA liner (which may be referred to as Liner #1) at 262, placing the lid 111 on a fixture (which may be referred to as Fixture #2) at 264, assembling Fixture #1 to Fixture #2 at 266, clamping and applying vacuum for a certain time and clamping pressure at 268, removing Fixture #1 at 270, removing a PSA liner (which may be referred to as Liner #2) at 272, inspecting for alignment at 274, aligning the lid to a case-back fixture at 276, clamping and applying vacuum for a certain time and clamping pressure at 278, and performing a final functional test at 280.

In various clinical or home healthcare settings, obtaining biometric data from patients can be advantageous, e.g. to sense levels of chemical compounds (e.g., glucose) in the tissue, to measure other characteristics (e.g., temperature) of the tissue, or to distinguish different kinds of tissue (e.g., to distinguish healthy tissue from diseased tissue).

Accordingly, in a first aspect, some embodiments provide a system comprising: a first module comprising a first sensor capable of performing biometric sensing at a first location on a patient; and a second module comprising a second sensor, capable of performing biometric sensing at a second location on the patient, wherein the first module comprises a transmitter for transmitting first sensor data, the first sensor data comprising sensing information obtained by the first sensor.

By having a first and second module which can perform biometric sensing at different locations on the patient, a number of advantages may be provided. For example, redundant measurements can be taken. Further, differential measurements of a same biomarker can be taken to enhance the fidelity of the signal (e.g., lower the signal-to-noise ratio), especially when calibrating with a known source. It can also provide insight into anatomical differences.

The system may have any one or, to the extent that they are compatible, any combination of the following optional features.

The first and/or second modules may form discreet subcomponents of a larger device or monitoring system. That is, the system may be a single device (including the first and second modules) or may be a monitoring system where the modules are provided in distinct devices. For example, the first and second modules may be discrete integrated circuits (electronic, photonic, or a mixture thereof) which are located within a patient monitoring system or device. In some examples the first and second modules are provided in separate devices which are capable of being independently positioned on the patient. For example, the first module may be located in one element worn or attached to the patient at a first location (e.g. in a wristband worn by the patient) whereas the second module may be located in another element worn or attached to the patient at a second location different to the first location (for example, an article of clothing, a chest strap, an earring, an ankle strap, an adhesive patch, an arm or biceps strap, or a ring).

The system may include further modules including sensors capable of performing biometric sensing at further locations on the patient. The system may form a distributed sensor network. The data from the sensors can be provided to a processing unit, which may be in one of the first or second modules or may be a separate module. The processing unit may be, or may be in, a third module or other module, for example a mobile device (e.g. cell phone, tablet, laptop, or other computer) which is in one- or two-way communication with the modules containing sensors. The processing unit may be a remote unit, for example in a cloud computing system connected to the modules via a network connection.

One of the modules may be deemed a main unit or main module and may control the other modules of the system. For example, it may prompt them to switch on or off and to take readings or perform calibration routines.

The modules may each include a plurality of sensors, or each sensor may be configured to undertake more than one type of biometric sensing. In either case, a wealth of biometric information is available allowing for multidimensional analysis across several factors.

One or more of the modules may be, or include, an optical sensing module or optical sensor. The or each optical sensing module or optical sensor may include a transmitter photonic integrated circuit, comprising a plurality of lasers where each laser of the plurality of lasers operates at a different wavelength from the others. The optical sensing module may include an optical manipulation region which can include one or more of: an optical modulator, an optical multiplexer, and additional optical manipulation elements. The module may include one or more optical outputs for light originating from the lasers. The optical sensing module may be, for example, as disclosed in WO 2021/116766 A1 the disclosure of which is incorporated by reference in its entirety.

In some examples, one or more of the sensors may be a photoplethysmography (PPG), speckleplethysmograph (SPG), or a spectrophotometer operating at one or more wavelength bands such as visible, near-infrared or short-wave infrared.

In one example, the optical sensors are provided on a top and bottom of a wristband (i.e., on a dorsal and ulnar/radial portion of the wristband) with electronic components disposed across the band. Positioning the sensors over the ulnar/radial portion of the patient's hand may enhance the data obtained by the sensors, for example because of the increased vascularization in that location as compared to (for example) the dorsal region of the patient's hand.

The system may further comprise a third module comprising a receiver, the third module being configured to receive the first sensor data and to combine the first sensor data with other sensor data. The third module may be the second module. The other sensor data may comprise sensing information obtained by the second sensor. The first module may comprise a receiver for receiving a signal from the second module.

The third module may be a mobile phone. The first module may comprise a receiver for receiving a signal from the third module. The other sensor data may comprise sensing information obtained by the second sensor.

The transmitter may be a wireless transmitter. The transmitter may be a Bluetooth remote therapeutic monitoring (RTM) transmitter or a WiFi (RTM) transmitter.

The first sensor or the second sensor may be capable of performing biometric sensing of a type selected from the group consisting of blood sugar measurements, blood glucose measurements, core body temperature measurements, hydration level measurements, blood pressure measurements, breathing rate measurements, SpO2 measurements, heart rate measurements, heart rate variability measurements and combinations thereof.

The first module may not include a receiver. In other words, the first module may be arranged to communicate in a one-way fashion with the second or third module by transmitting to them but being unable to receive information from them. In some examples the second module does not include a receiver.

The first sensor and the second sensor may be configured to perform redundant measurements. That is, the first and second sensor may be configured to perform biometric sensing of a same type.

The first and second modules may be located within a wearable device. In this sense, the system may be considered a wearable device. The wearable device may be or include a wristband, and the first and second modules may be located at different circumferential positions around the wristband (i.e., at different points around a circumference of the wristband, the wristband having a generally circular or ovoidal shape or surface). The wristband may include a clasp or other fixing mechanism which can be coupled or uncoupled so as to form a complete or split band respectively. The clasp or other fixing mechanism may be used to form electrical connections between components in or on the wristband.

The system may further include an indicator module, configured to provide feedback to a user as to the position of the wearable medical device on the user. The indicator module may be, for example, a plurality of LEDs which illuminate to indicate that the wearable medical device is positioned at predetermined location on the user. The system may further include an adjustment mechanism to vary a dimension of the medical device. The wearable medical device may be a wristband, including, or being connectable to, a watch module configured to display the time, the wristband being arranged such that the watch module is or would be disposed on a dorsal portion of a wristband and the first and second modules are disposed on a radial or ulnar portion of the wristband. By dorsal portion, it is typically meant the upper portion of the wrist on the same side of the hand as the fingernails. Whereas the radial or ulnar portions are located circumferentially around the wrist, on a lower portion, e.g., on the same side as the palm of the hand. The wearable device may include a flexible battery unit.

The system may further include a notification module, configured to feed back to a user a value of a biomarker derived from the sensor data. For example, the notification module may provide haptic or visual feedback (e.g., through a vibrator or LED) that a value of a biomarker is outside of a predetermined range or exceeding a predetermined threshold.

The watch module may include one or more transmitters for connecting and communicating with another device, such as a mobile phone.

The wristband may be formed of a flexible material (e.g., rubber), or formed of a plurality of links of a relatively inflexible material (but so as to be conformed as a device to a shape of the patient by virtue of the movable links). The wristband may be, for example, about 3 mm in thickness and may be about 20 mm wide.

The first sensor and the second sensor may be configured to perform biometric sensing of a same type on different locations of the patient. One or both of the first module and the second module may be configured to derive a biomarker value from sensor data from both the first sensor and the second sensor. In some examples, a differential measurement is taken which may include determining a difference between the biomarker value as derived from the sensor data of the first sensor and the biomarker value as derived from the sensor data of the second sensor. For example, the system may determine a first blood pressure measurement at a point proximal to the heart of the patient using the first sensor and a second blood pressure measurement from a point distal to the heart of the patient using the second sensor. The system may be able to determine, therefore, from a difference between the first and second blood pressure measurements that the patient may have poor blood circulation or perfusion.

One or both of the first module and the second module may be configured to receive sensor data from both the first sensor and the second sensor, and to derive a biomarker value from the sensor data from only one first and second sensor. The relevant module may examine the sensor data from the first sensor and the second sensor and choose to derive the biomarker value form the sensor data with the highest quality.

Figure 3:
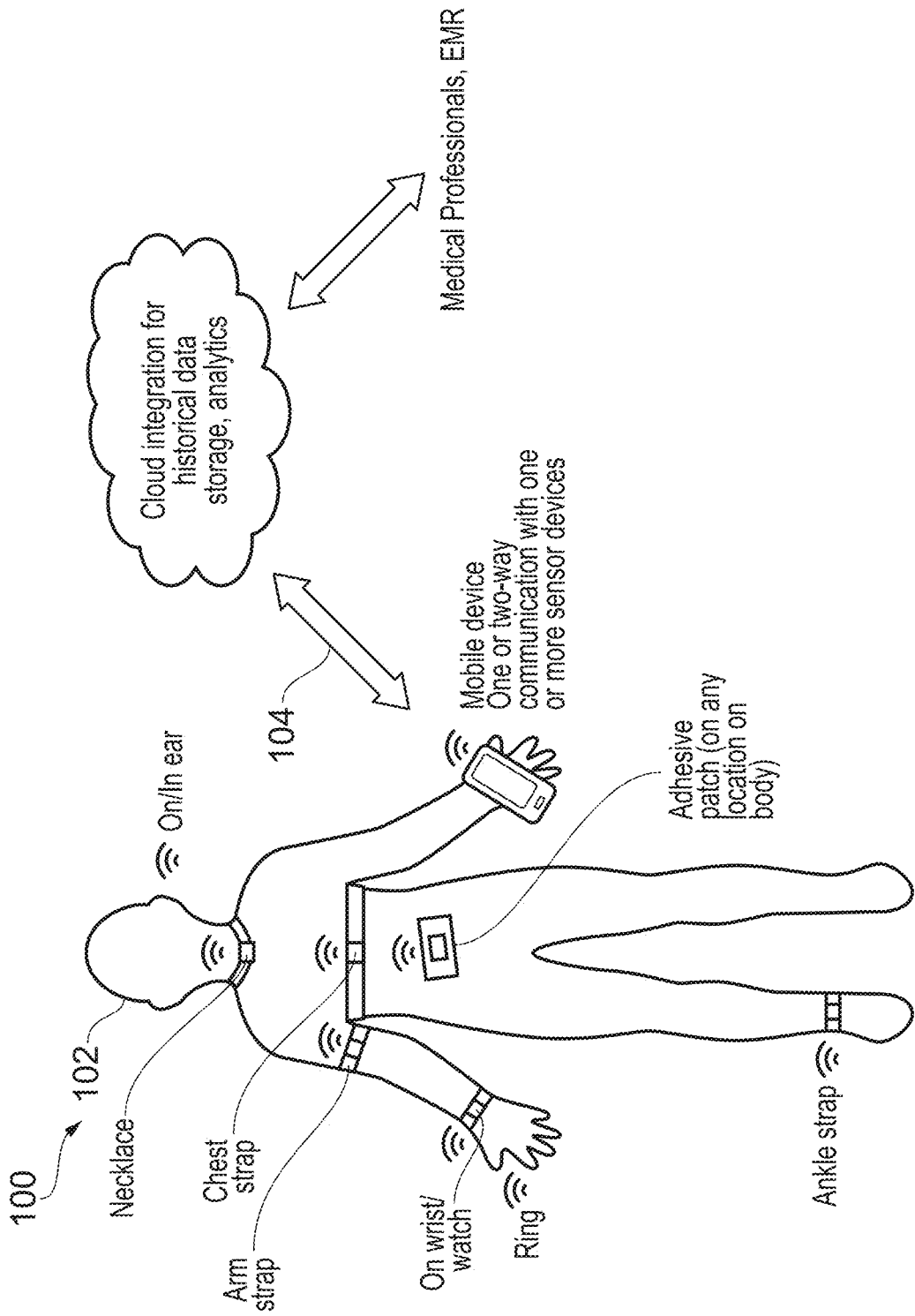
FIG. 3 shows a system, according to an embodiment of the present disclosure.

FIG. 3 shows a system 100. The system includes a first module comprising a first sensor, capable of performing a biometric sensing at a first location on a patient. In the system shown in FIG. 3, the first module is one of: a necklace; a chest strap; an earring; a device worn in the inner-ear; a wristband/watch; a ring; an ankle strap; an adhesive patch located on the body; an arm or biceps strap; or a mobile device. The second module is another of a chest strap; an earring; a wristband/watch; a ring; an ankle strap; an adhesive patch located on the body; an arm or biceps strap; or a mobile device. For example, the first module may be a wrist strap and the second module may be a chest strap. The first module includes a transmitter for transmitting first sensor data, where the first sensor data includes sensing information obtained by the first sensor.

The sensors in the first module and second module, as described above, are configured to (and so capable of) performing biometric sensing at their respective locations on the patient. The sensors can be configured to sense: blood sugar level; blood glucose level; core body temperature; hydration level; blood pressure; breathing rate; SpO2 level; heart rate; heart rate variability, and combinations thereof. The sensors may do so by including photonic components, for example in a small form factor photonic integrated circuit (PIC), as combined with an application specific integrated circuit and/or flexible electronic substrate. The PIC can include, for example, two or three lasers with different wavelengths in the red and near infrared ranges by combining SPG and PPG data.

Where a mobile device forms a part of the system, it can be in one- or two-way communication with the other module(s) including the other sensor(s). For example, the module(s) including the other sensor(s) may be configured to transmit only to the mobile device and may not be able to receive signals from the mobile device.

The mobile device can process the received sensor data to derive biometric markers (e.g., heart rate, glucose level, etc.). Additionally or alternatively, the sensor data can be transmitted to a cloud computing system for cloud integration facilitating historical data storage and more powerful analytical techniques than might be executable on a mobile device. The data can also be shared with medical professionals, either directly or through use of an electronic medical records (EMR) system. This can be implemented either via the cloud (as shown) or directly from the mobile device.

Figure 4:
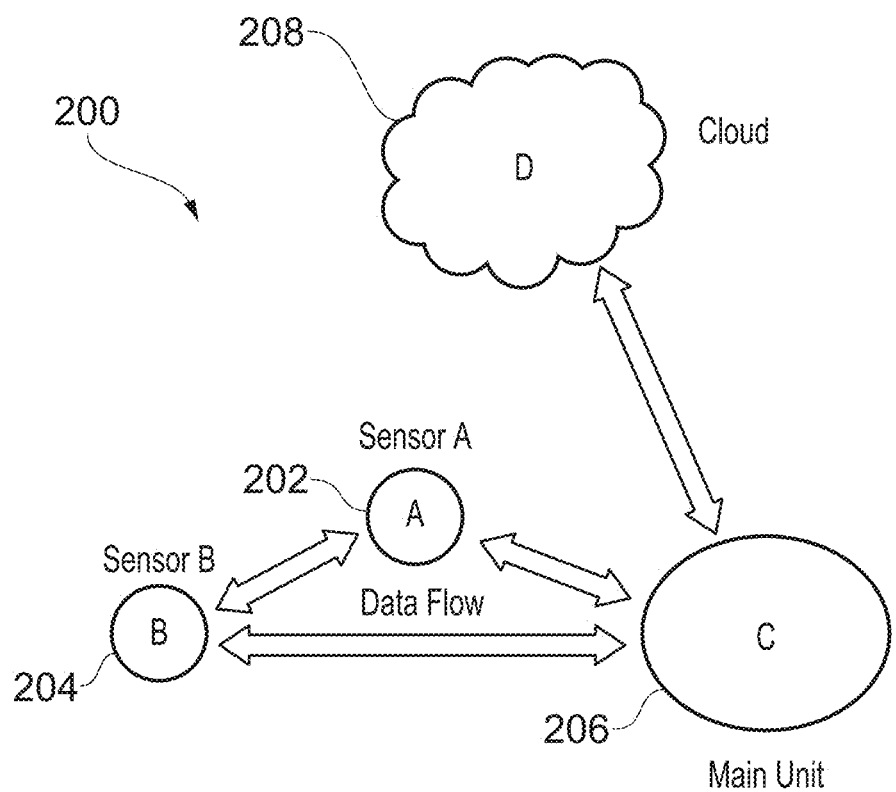
FIG. 4 shows a variant system, according to an embodiment of the present disclosure.

FIG. 4 shows a schematic diagram of a system 200 including three modules. A first module 202 includes sensor A which is configured to perform biometric sensing. A second module 204 includes sensor B which is also configured to perform biometric sensing. A third module 206, termed the main unit, is in communication with the first module 202 and second module 204 (which are also in communication with one another). The third module may contain a sensor configured to perform biometric sensing, or may not and may function instead as a processing or communication unit only. In this example the third module 206 is connected to a cloud computing system 208 of the type discussed previously, which may perform further analytical techniques or storage of the data obtained from the sensors.

In some examples, the sensors in each module are configured to sense different kinds of biometric data (for example from the list discussed above) or they may be configured to sense the same kind of biometric data, or subsets of the sensors may be configured to sense the same kind of biometric data whilst yet other sensors or subsets of sensors are configured to sense different kinds of biometric data. Each module may include more than one sensor and so the different sensors within a module may respectively sense different kinds of biometric data.

In examples where the sensors of respective modules are configured to sense the same biometric data, the main unit may decide which data to use between the data from the different sensors based on a quality score or other ranking. The main unit may also be configured to utilize the data from both (or all) sensors in the derivation of a given biometric marker. This can be done, for example, through use of differential analysis to provide enhanced accuracy for a given biomarker or to investigate the change in a biomarker as a function of anatomical position.

Additionally or alternatively the sensors may perform redundant measurements (i.e. both recording the same kind of data in case one or the other fails during a given data acquisition run).

Figure 5:
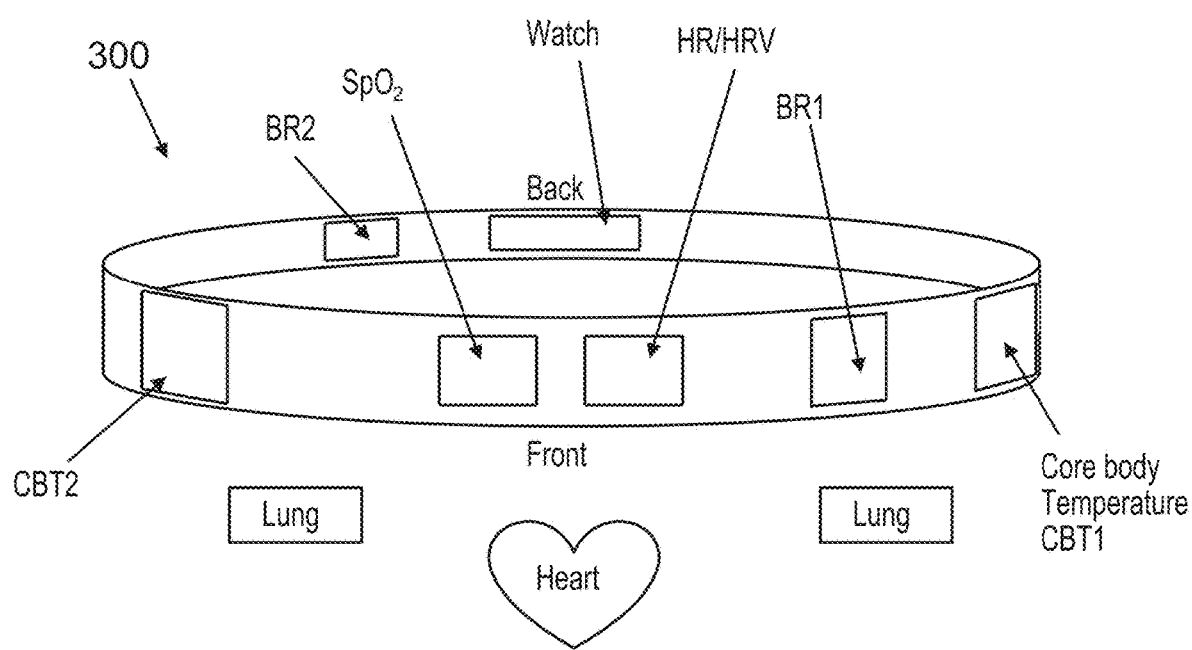
FIG. 5 shows a wearable device, according to an embodiment of the present disclosure.

FIG. 5 shows a wearable device 300. In this example, the wearable device 300 is a wristband suitable to be worn around the wrist of a patient. The wristband includes a number of sensors, for example breathing rate sensor 1 (BR1), breathing rate sensor 2 (BR2), core body temperature 1 sensor (CB1), core body temperature 2 sensor (CB2), saturation percentage of oxygen sensor (SpO2), and heart rate/heart rate variability sensor (HR/HRV).

In this example the wearable device includes a watch module which is configured to display the time. The watch module is located on a back side of the wearable device, which corresponds to the dorsal region of the wristband and so the dorsal portion of the patient when the wristband is on the patient. Whereas at least some of the sensors (which may be included in their own modules) are located on a radial or ulnar portion of the wristband to enhance data collection. The watch module, in this example, includes a transmitter (e.g., a Bluetooth (RTM) transmitter) for transmitting the data from the sensors.

Figure 6:
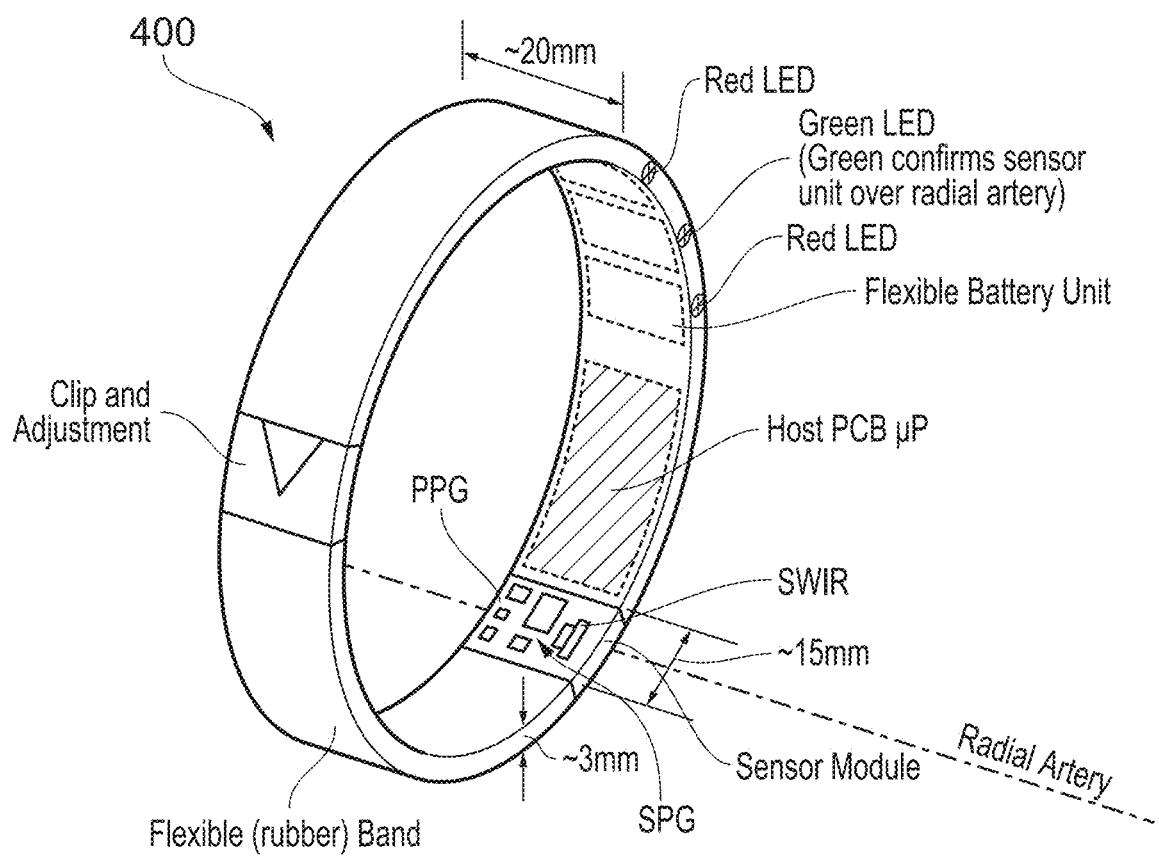
FIG. 6 shows a variant wearable device, according to an embodiment of the present disclosure.

FIG. 6 shows a variant wearable device 400. This wearable device 400 is also a wristband, which is about 20 mm wide (i.e., as measured in a direction aligned with the arm of the patient when worn) and is about 3 mm thick (as measured in a radial direction of the wristband). The wristband 400 includes a clip and adjustment mechanism, so that the ring formed by the wristband can be broken or closed by use of the clip or clasp, and the radius or circumference of the wristband can be varied through use of the adjustment mechanism. In some examples the clip or clasp includes electrical connectors which connect components of the wristband when closed.

The wristband 400 in this example is formed from a flexible material, such as rubber, so as to conform to the shape of the patient's wrist. In other examples, not shown, the wristband is formed of a plurality relatively inflexible links or elements which are connected together so as to be respectively pivotable. In this manner, the wristband can still conform to the shape of the patient's wrist whilst not being formed of a flexible material.

The wristband 400 in this example includes an indicator unit to notify the user if they have placed the wristband in a correct predetermined position on their person. For example, the wristband 400 in this example includes a module which includes a PPG sensor, SWIR sensor, and SPG sensor. The indicator unit notifies the user if these sensors have been positioned above the patient's radial artery, for example by illuminating one or more red LEDs (light emitting diodes) when the unit is incorrectly positioned and illuminating one or more green LEDs when the unit is correctly positioned. The wristband 400 includes a flexible battery unit, as well as a host PCB which can provide the third module. The sensor module in this example includes the SWIR sensor, SPG sensor, and PPG sensor.

Figure 7A:
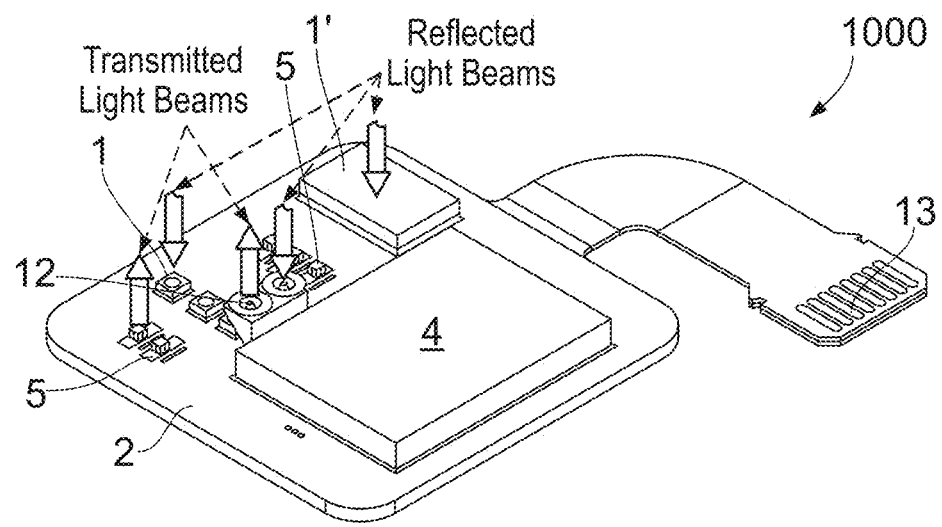
FIG. 7A shows a front view of an optical sensing module, according to an embodiment of the present disclosure.

In some embodiments, the sensing module 105 comprises a portion of an optical sensing subassembly 1000 discussed with reference to FIGS. 7A-8. The optical sensing subassembly 1000 includes a transmitter photonic integrated circuit (PIC) 4 located on a substrate 2. The PIC 4 includes a plurality of lasers, each laser of the plurality of lasers operating at a wavelength that is different from the wavelength of the others. The plurality of lasers form part of a light source 20 generating light in the range 1200 nm to 2400 nm. The plurality of lasers can also be configured for variable duty-cycle operation. The interrogating laser light may be varied in amplitude, phase, polarization, or in other optical properties or a combination of such optical properties. Pulsing of the light can reduce the power consumption of the device and lead to longer battery life.

The PIC 4 also includes an optical manipulation region for manipulating the light in any way required prior to transmission via one or more optical outputs 12 to the surface (e.g., tissue) to be analyzed. An optical element such as a mirror 15 (e.g., prism mirror) may be present. The optical manipulation region includes one or more of: an optical modulator, optical multiplexer (MUX); and additional optical manipulation elements such as power taps, lenses and power splitters.

In this example, the light source 20 also includes a plurality of non-laser light sources such as LEDs 5 (e.g., visible LEDs 5a or near infrared wavelength LEDs 5b).

One or more photodetectors 1, 1' also form part of the optical sensing subassembly 1000. Here, the photodetectors are located on the substrate 2 but are not part of the PIC 4. However, it is envisaged that the photodetectors could be located as an integral part of the transmitter/receiver PIC 4. In this example, the plurality of photodetectors includes silicon photodiodes 1' and InGaAs photodiodes 1.

A microcontroller 11 is located on the back side of substrate 2 of the optical sensing subassembly 1000, i.e., opposite the PIC 4. Electrical connector 13 provides electrical signals to the optical sensing subassembly, and a protective casing 7 (shown in FIG. 7C), including a lid and a base, acts to cover the PIC 4 and other components to minimize the risk of damage during use. In the example of FIG. 8, the optical sensing subassembly 1000 includes a large area detector array comprising smaller photodetector pixels 1106, which is seen in FIG. 9.

The operation of the optical sensing subassembly 1000 is described with reference to FIG. 9. Once manipulated (e.g., multiplexed), light from the plurality of lasers exits the PIC 4 and therefore the optical sensing subassembly 1000 via one or more optical output ports 12. Light may be launched into free space from a waveguide facet (a "launch facet") at or near the edge of the PIC 4. An optical element such as a mirror 15 takes the light from the plane of the waveguide platform and translates it into a direction more suitable for interrogating a sampled tissue (e.g., user's skin). The direction (see transmitted/reflected light beam) may be orthogonal or substantially orthogonal to the plane of the PIC 4.

Back-scattered light (see reflected light beams) from the surface of the skin, and from within a volume below the surface of the skin, returns to the launch facet (or, in some embodiments, a different waveguide facet) on the PIC 4 to be analyzed. Specifically, the reflected light returns to the PIC 4 to illuminate the respective active areas of the photodiodes 1, 1' and/or photodetector pixels 1106.

Figure 7B:
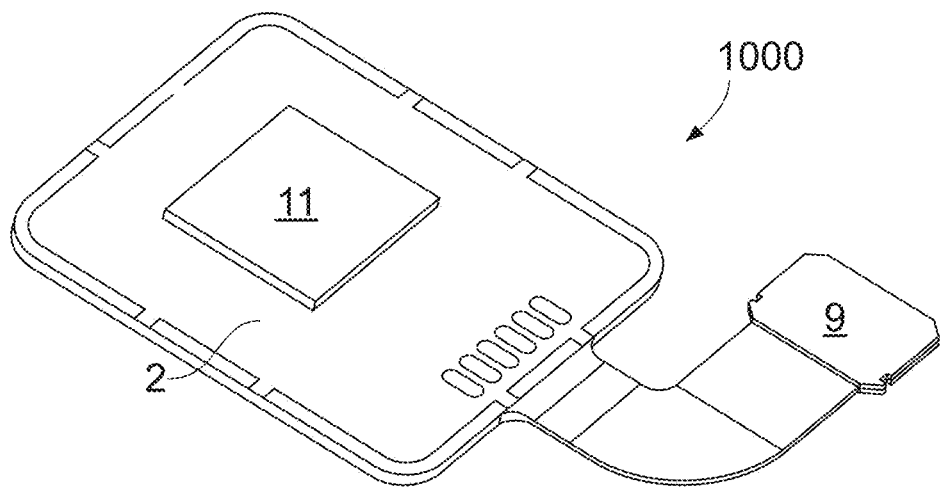
FIG. 7B shows a back view of an optical sensing module, according to an embodiment of the present disclosure.
Figure 7C:
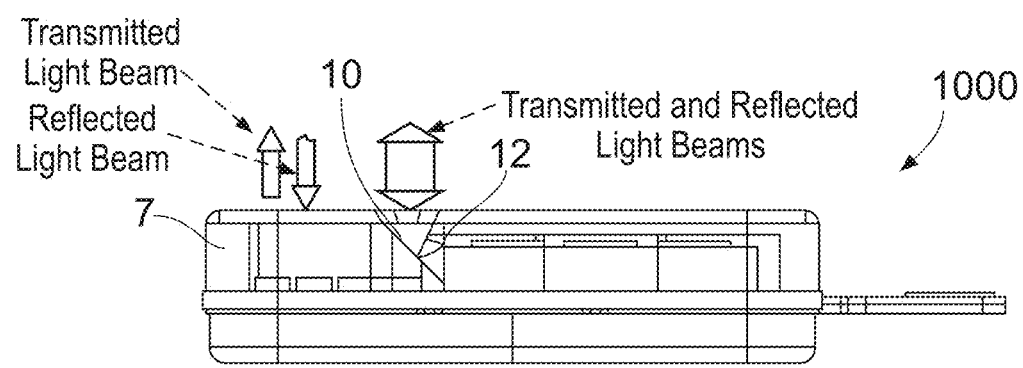
FIG. 7C shows a cross-sectional view of an optical sensing module, according to an embodiment of the present disclosure.
Figure 8:
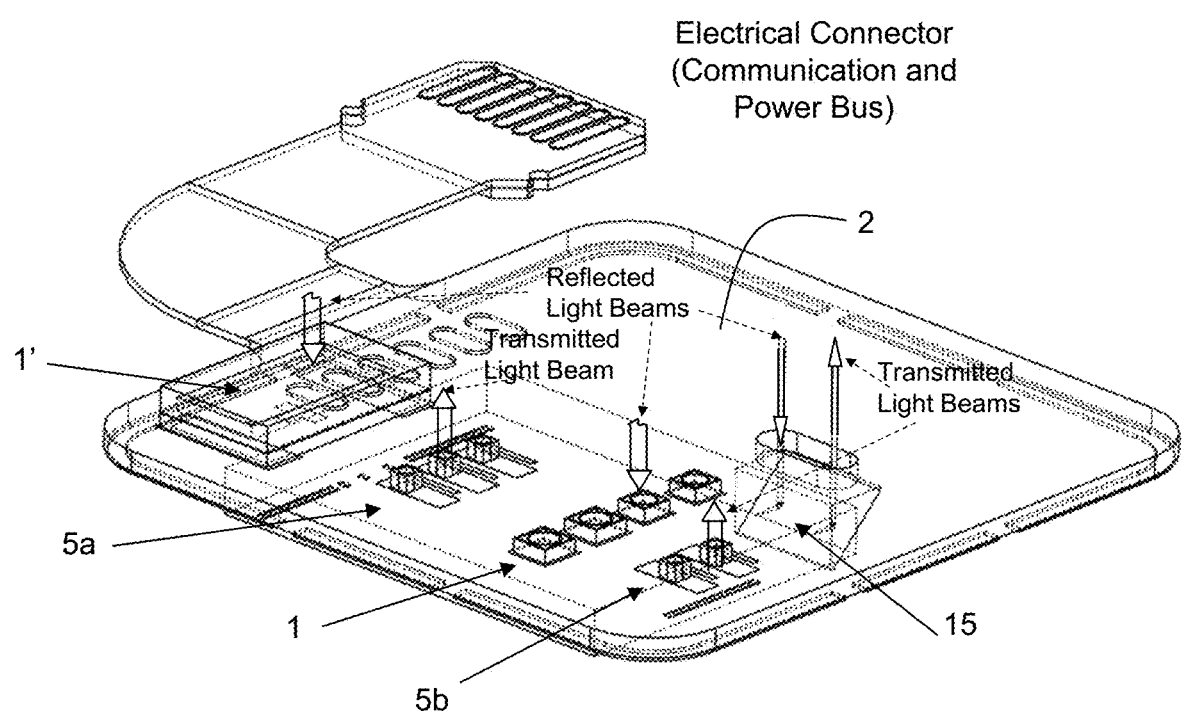
FIG. 8 shows the optical sensing module of FIGS. 7A-7C with an incorporated reflecting mirror.
Figure 9:
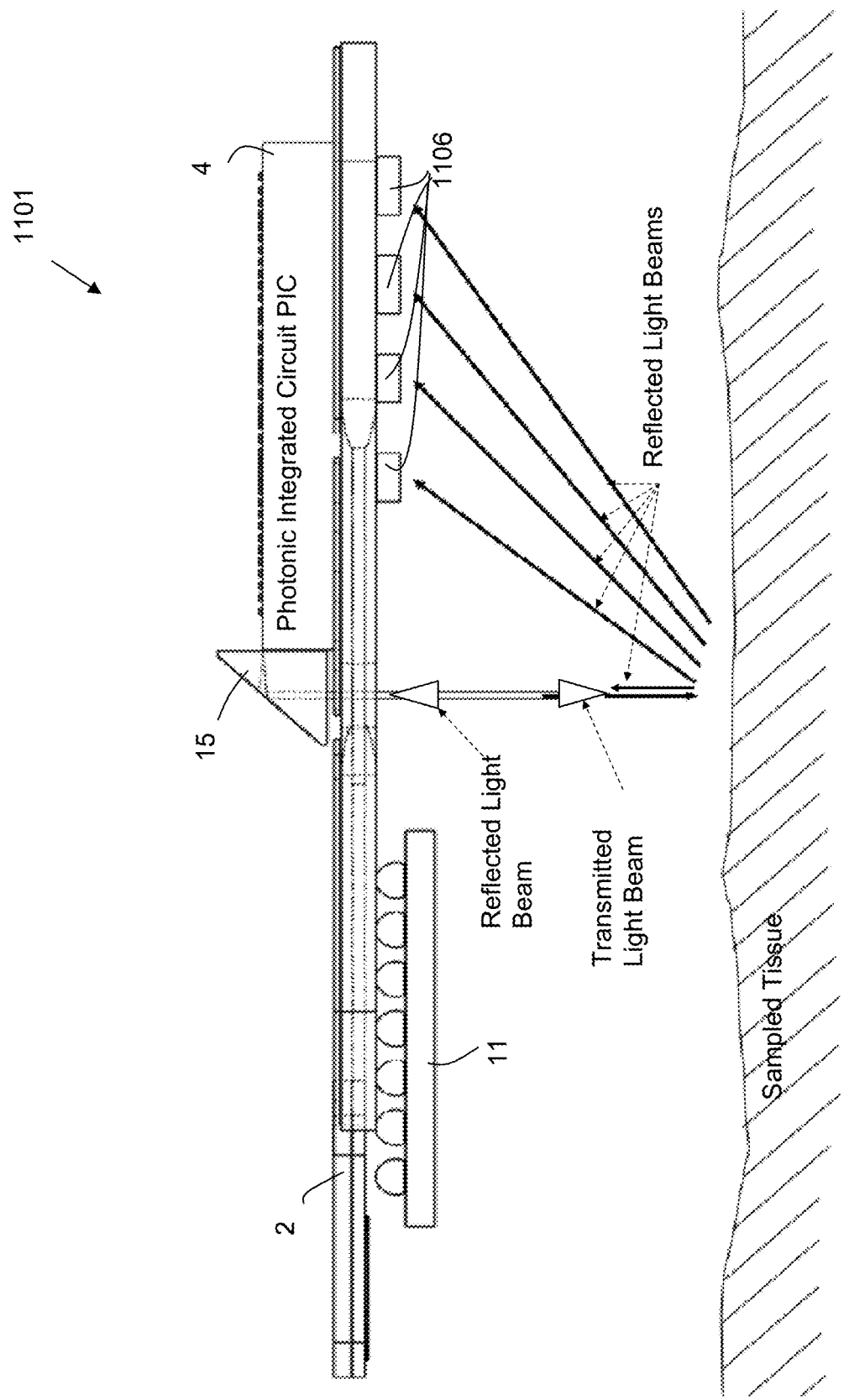
FIG. 9 shows the optical sensing module of FIG. 8 in operation.
Figure 10:
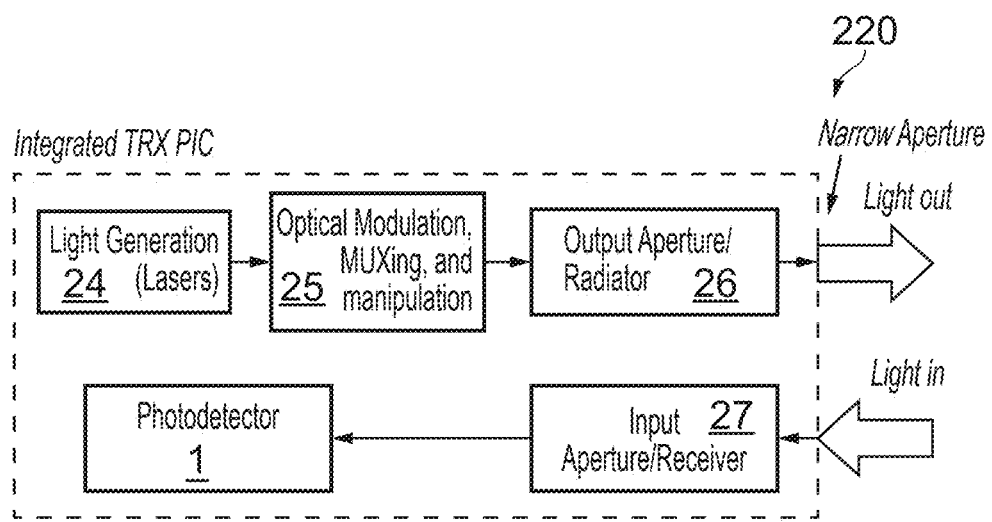
FIG. 10 schematically shows a variant of the optical sensing module of FIGS. 7A-8 comprising a single transmitter/receiver PIC with integrated photodetectors.

FIG. 10 is a block diagram schematically showing a variant of the optical sensing subassembly of FIGS. 7-8 comprising a single transmitter/receiver PIC 4 with an integrated photodetector 1, such as a photodiode 1. In relation to the transmitter functionality, the plurality of lasers 24 provides light of different wavelengths to the optical manipulation region 25 before being output at the one or more optical outputs 26. In relation to the receiver functionality, light is received at one or more input apertures 27 which are optically coupled to the photodiode 1.

Figure 11:
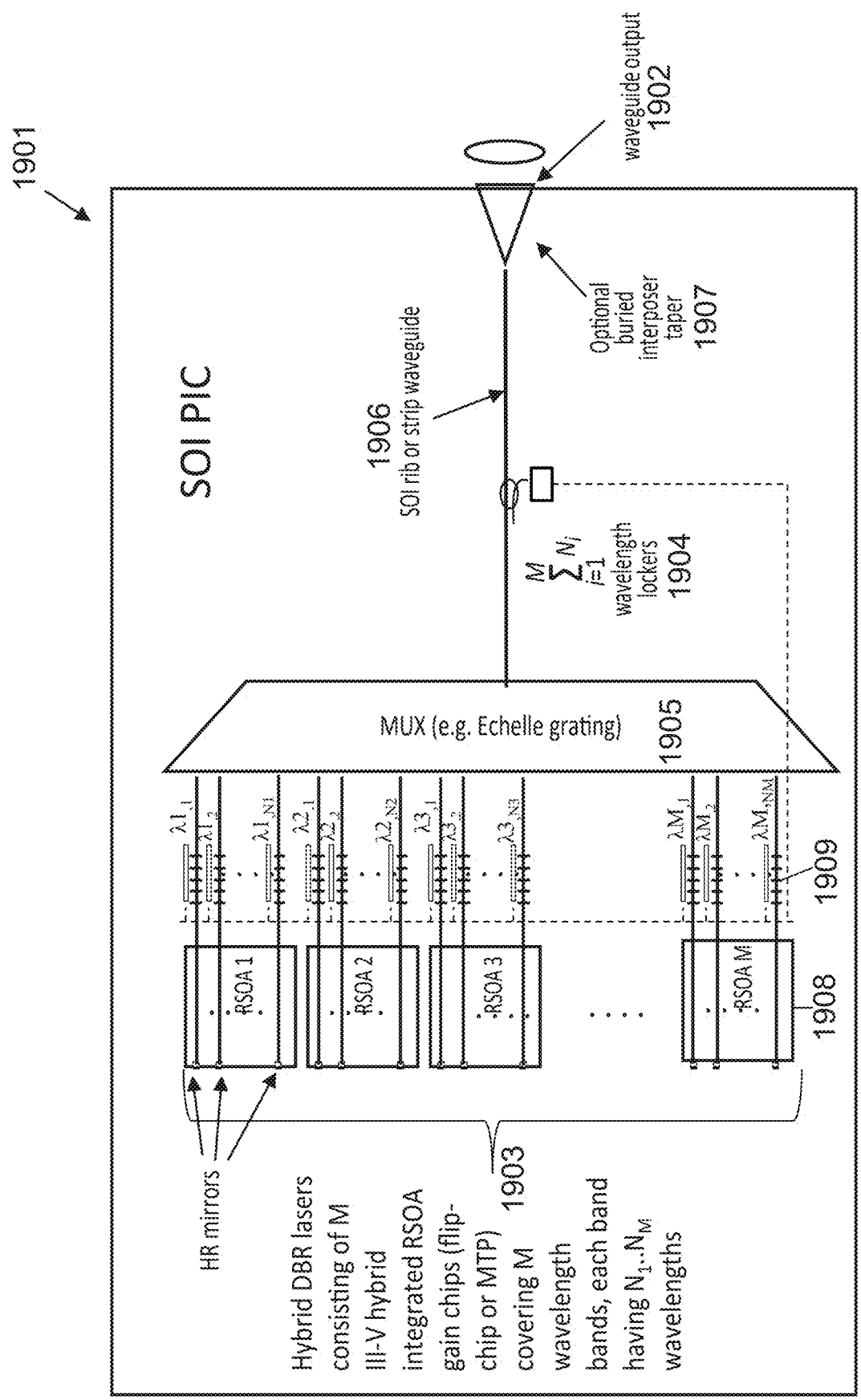
FIG. 11 is an example of a transmitter PIC with a single output aperture which may form part of an optical sensing module.

FIG. 11 is an example of a transmitter PIC 1901 with a single waveguide output aperture 1902 which may form part of an optical sensing subassembly 1000 for non-invasive biomarker measurement. Here, the plurality of lasers takes the form of a plurality of hybrid DBR lasers 1903 including M III-V hybrid integrated RSOA gain chips or coupons 1908 (mounted by flip-chip or micro transfer printed (MTP)) covering M wavelength bands, each band having 1 . . . N wavelengths. Each of the M RSOAs is optically coupled to N DBR waveguides, each DBR waveguide 1909 selecting a sub-band within the wavelength band of the RSOA to give rise to N wavelengths within each of the M wavelength bands. The total number of output wavelengths from the plurality of lasers is therefore NxM. For each laser, highly reflective mirrors are located at one end of the laser cavity, within the RSOA. The III-V RSOA gain chips or coupons can be hybrid integrated such that the optical mode in the RSOA waveguide is edge-coupled to the Si or SiN PIC waveguide, such that the light in the RSOAs and the light in the Si or SiN PIC waveguides stay in the same plane (see A. J. Zilkie et al., Power-efficient III-V/Silicon external cavity DBR lasers, et al., Optics Express, Vol 20, (21) page 23456 (2012); A. J. Zilkie et al., Multi-Micron Silicon Platform for Highly Manufacturable and Versatile Photonic Integrated Circuits, IEEE J. Sel. Topics in Quantum Electronics, Vol 25, (5) (2019); both of which are incorporated herein by reference). In one example, only one laser is turned on in each time window, and in that time window the photodiode 1 detects the reflected signal from that wavelength. The lasers are then cycled through. The PIC shown in FIG. 11 has an SOI platform. The same architecture could also be applied on a SiN platform, the choice of waveguide platform depending on the wavelengths of operation of the lasers. It may be envisaged that a single platform may include SOI and SiN components.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, the word "or" is inclusive, so that, for example, "A or B" means any one of (i) A, (ii) B, and (iii) A and B.

As used herein, the term "major component" refers to a component that is present in a composition, polymer, or product in an amount greater than an amount of any other single component in the composition or product. In contrast, the term "primary component" refers to a component that makes up at least 50% by weight or more of the composition, polymer, or product. As used herein, any structure or layer that is described as being "made of" or "composed of" a substance should be understood (i) in some embodiments, to contain that substance as the primary component or (ii) in some embodiments, to contain that substance as the major component.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a wearable device have been specifically described and illustrated herein, many modifications and variations will be apparent to those skilled in the art. Accordingly, it is to be understood that a wearable device constructed according to principles of this disclosure may be embodied other than as specifically described herein. The invention is also defined in the following claims, and equivalents thereof.

What is claimed is:

1. A wearable device, comprising:
   a housing having a first window in a lower surface of the housing, the lower surface at least in part defining a user-contact surface;
   a partially transparent element disposed within the first window protruding from the lower surface;
   a sensing module comprising a transmitter photonic integrated circuit and configured to obtain biometric data when worn by a user, the biometric data configured for optical sensing of a concentration of a chemical compound within tissue of the user through the partially transparent element; and
   a strap attached to the sensing module,
   the wearable device being configured to be worn by the user,
   the strap extending over an upper surface of the housing.

2. The wearable device of claim 1, wherein the wearable device is configured to be worn on a wrist of the user.

3. The wearable device of claim 1, wherein a portion of the strap is composed of an elastomer.

4. The wearable device of claim 3, wherein the portion of the strap is pre-formed to conform to the upper surface of the sensing module and to two sides of the sensing module.

5. The wearable device of claim 1, wherein a portion of the strap is a fabric band.

6. The wearable device of claim 5, wherein a portion of the strap is an elastic fabric band.

7. The wearable device of claim 5, wherein the strap is configured to slide longitudinally relative to the sensing module.

8. The wearable device of claim 7, wherein:
   the wearable device is configured to be worn on a wrist of the user; and
   the wearable device is configured to accommodate a wrist circumference of 6.8 inches.

9. The wearable device of claim 7, wherein:
   the wearable device is configured to be worn on a wrist of the user; and
   the wearable device is configured to accommodate a wrist circumference of 6.0 inches.

10. The wearable device of claim 1, wherein the sensing module comprises:
    a first strap slot, on a first side of the sensing module; and
    a second strap slot, on a second side of the sensing module, opposite the first side.

11. The wearable device of claim 1, further comprising an electrical connector, wherein:
    the housing further has a second window in the lower surface of the housing; and
    the electrical connector is in the second window.

12. The wearable device of claim 1, wherein the partially transparent element is a glass-to-metal assembly comprising:
- a metal disk having a first window, and
- a first glass window, covering the first window of the metal disk.

13. The wearable device of claim 12, wherein:
- the first glass window does not protrude below a lower surface of the metal disk by more than 100 microns, and
- the first glass window is not recessed within the metal disk by more than 200 microns.

14. The wearable device of claim 12, wherein a portion of the first glass window has a speckle contrast parameter of less than 0.7.

15. The wearable device of claim 12, wherein:
- the glass-to-metal assembly further comprises a second glass window;
- the metal disk further has a second window; and
- the second glass window covers the second window of the metal disk.

16. The wearable device of claim 15, wherein:
- the glass-to-metal assembly has a first wall, the first wall being a portion of a partition separating a light emitting region of the sensing module from a light detecting region of the sensing module;
- the first window of the metal disk opens into the light emitting region; and the second window of the metal disk opens into the light detecting region.

17. The wearable device of claim 12, wherein the sensing module further comprises a sensor printed circuit board assembly, on the partially transparent element, the sensor printed circuit board assembly comprising a spectrophotometer configured to illuminate the skin of the user with light transmitted through a first transparent portion of the partially transparent element and to detect light returning, through a second transparent portion of the partially transparent element, to a photodetector of the spectrophotometer after transmission through tissue of the user.

18. The wearable device of claim 17, wherein the sensing module further comprises:
- a battery carrier, on the sensor printed circuit board assembly; and
- a battery, on the battery carrier,
- wherein the battery carrier is configured to protect the battery from damage by components, of the sensing module, below the battery.

* * * * *